United States Patent
Yoshida

(10) Patent No.: US 10,076,298 B2
(45) Date of Patent: Sep. 18, 2018

(54) IMAGE PROCESSING SYSTEM AND IMAGE PROCESSING DEVICE

(71) Applicant: KONICA MINOLTA, INC., Chiyoda-ku, Tokyo (JP)

(72) Inventor: Junko Yoshida, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 273 days.

(21) Appl. No.: 15/008,284

(22) Filed: Jan. 27, 2016

(65) Prior Publication Data
US 2016/0253785 A1    Sep. 1, 2016

(30) Foreign Application Priority Data

Feb. 26, 2015   (JP) .................................. 2015-036006

(51) Int. Cl.
*A61B 6/00*   (2006.01)
*G06T 5/00*   (2006.01)
*G06T 5/50*   (2006.01)

(52) U.S. Cl.
CPC ............ *A61B 6/484* (2013.01); *A61B 6/4035* (2013.01); *A61B 6/52* (2013.01); *A61B 6/5205* (2013.01); *G06T 5/008* (2013.01); *G06T 5/50* (2013.01); *A61B 6/505* (2013.01); *G06T 2207/10116* (2013.01); *G06T 2207/20224* (2013.01); *G06T 2207/30008* (2013.01)

(58) Field of Classification Search
CPC ....... A61B 6/4035; A61B 6/484; A61B 6/505; A61B 6/52; A61B 6/5205
USPC ...................................................... 378/62, 36
See application file for complete search history.

(56) References Cited

U.S. PATENT DOCUMENTS

| 7,433,444 | B2 * | 10/2008 | Baumann | ............... | A61B 6/032 378/145 |
| 7,453,981 | B2 * | 11/2008 | Baumann | ............... | A61B 6/484 378/21 |
| 7,486,770 | B2 * | 2/2009 | Baumann | ............... | A61B 6/032 378/145 |

(Continued)

FOREIGN PATENT DOCUMENTS

JP        2014135989 A      7/2014

*Primary Examiner* — Allen C. Ho
(74) *Attorney, Agent, or Firm* — Holtz, Holtz & Volek PC

(57) ABSTRACT

A medical image system includes: X-ray equipment having a Talbot interferometer or a Talbot-Lau interferometer and including: an X-ray source configured to emit X-rays; a plurality of gratings arranged in a emitting direction of the X-rays; and an X-ray detector irradiated by the X-ray source and having conversion elements for accumulating charge and generating electrical signal to read the electrical signals generated to acquire moire fringe image; a subject absorption image generation unit configured to generate a subject absorption image based on moire fringe images containing a subject; a subjectless absorption image generation unit configured to generate a subjectless absorption image based on subjectless more fringe images; and an image unevenness correction unit configured to correct image unevenness of the subject absorption image, the medical image system further including a subjectless absorption image correction unit, wherein the image unevenness correction unit corrects image unevenness of the subject absorption image.

7 Claims, 12 Drawing Sheets

(56) References Cited

U.S. PATENT DOCUMENTS

| | | | | |
|---|---|---|---|---|
| 7,492,871 | B2* | 2/2009 | Popescu | A61B 6/00 378/145 |
| 7,522,698 | B2* | 4/2009 | Popescu | A61B 6/032 378/19 |
| 7,522,708 | B2* | 4/2009 | Heismann | A61B 6/00 378/145 |
| 7,564,941 | B2* | 7/2009 | Baumann | A61B 6/484 378/146 |
| 7,639,786 | B2* | 12/2009 | Baumann | A61B 6/484 378/145 |
| 7,646,843 | B2* | 1/2010 | Popescu | A61B 6/032 356/521 |
| 7,746,981 | B2* | 6/2010 | Takahashi | G01T 1/2928 250/370.11 |
| 7,889,838 | B2* | 2/2011 | David | A61B 6/4233 378/36 |
| 7,924,973 | B2* | 4/2011 | Kottler | G01B 15/025 378/36 |
| 7,945,018 | B2* | 5/2011 | Heismann | A61B 6/032 378/145 |
| 8,041,004 | B2* | 10/2011 | David | A61B 6/484 378/36 |
| 8,094,776 | B2* | 1/2012 | Takahashi | A61B 6/025 378/21 |
| 8,139,711 | B2* | 3/2012 | Takahashi | A61B 6/00 356/457 |
| 8,184,771 | B2* | 5/2012 | Murakoshi | A61B 6/484 378/145 |
| 8,233,587 | B2* | 7/2012 | Sato | G21K 1/06 378/36 |
| 8,280,000 | B2* | 10/2012 | Takahashi | A61B 6/484 378/62 |
| 8,411,816 | B2* | 4/2013 | Ohara | A61B 6/484 378/36 |
| 8,451,975 | B2* | 5/2013 | Tada | A61B 6/4291 378/207 |
| 8,515,002 | B2* | 8/2013 | Huang | B82Y 10/00 378/6 |
| 8,576,983 | B2* | 11/2013 | Baeumer | G21K 1/06 378/145 |
| 8,591,108 | B2* | 11/2013 | Tada | A61B 6/00 378/207 |
| 8,632,247 | B2* | 1/2014 | Ishii | A61B 6/00 378/207 |
| 8,755,487 | B2* | 6/2014 | Kaneko | A61B 6/06 378/36 |
| 8,767,915 | B2* | 7/2014 | Stutman | G01N 23/04 378/62 |
| 8,767,916 | B2* | 7/2014 | Hashimoto | A61B 6/484 378/62 |
| 8,781,069 | B2* | 7/2014 | Murakoshi | A61B 6/4233 378/36 |
| 8,824,629 | B2* | 9/2014 | Ishii | G01N 23/04 378/62 |
| 8,855,265 | B2* | 10/2014 | Engel | A61B 6/00 378/36 |
| 8,903,042 | B2* | 12/2014 | Ishii | A61B 6/4233 378/207 |
| 8,989,347 | B2* | 3/2015 | Sperl | G01N 23/046 250/370.08 |
| 8,989,474 | B2* | 3/2015 | Kido | A61B 6/4291 382/132 |
| 8,995,614 | B2* | 3/2015 | Nagatsuka | A61B 6/463 378/62 |
| 9,001,969 | B2* | 4/2015 | Murakoshi | A61B 6/4233 378/70 |
| 9,014,333 | B2* | 4/2015 | Sperl | A61B 6/484 378/132 |
| 9,025,725 | B2* | 5/2015 | Kiyohara | A61B 6/06 378/197 |
| 9,025,726 | B2* | 5/2015 | Ishii | A61B 6/484 378/62 |
| 9,036,773 | B2* | 5/2015 | David | A61B 6/4035 378/36 |
| 9,044,154 | B2* | 6/2015 | Hoshino | A61B 6/04 |
| 9,084,528 | B2* | 7/2015 | Geller | A61B 6/00 |
| 9,107,638 | B2* | 8/2015 | Hoshino | A61B 6/484 |
| 9,134,259 | B2* | 9/2015 | Huang | A61B 6/484 |
| 9,329,141 | B2* | 5/2016 | Stutman | G01N 23/046 |
| 9,330,456 | B2* | 5/2016 | Sperl | G06T 7/0012 |
| 9,472,007 | B2* | 10/2016 | Maack | G06T 11/60 |
| 9,510,799 | B2* | 12/2016 | Makifuchi | A61B 6/4291 |
| 9,597,050 | B2* | 3/2017 | Roessl | A61B 6/484 |
| 9,629,600 | B2* | 4/2017 | Hoshino | A61B 6/484 |
| 9,665,950 | B2* | 5/2017 | Kiyohara | G06T 11/00 |
| 9,672,949 | B2* | 6/2017 | Makifuchi | G21K 1/067 |
| 9,775,575 | B2* | 10/2017 | Proksa | G01N 23/046 |
| 9,839,407 | B2* | 12/2017 | Roessl | A61B 6/582 |
| 9,855,018 | B2* | 1/2018 | Hamano | A61B 6/566 |
| 9,861,330 | B2* | 1/2018 | Rössl | A61B 6/484 |
| 2014/0198895 | A1 | 7/2014 | Hoshino et al. | |

* cited by examiner

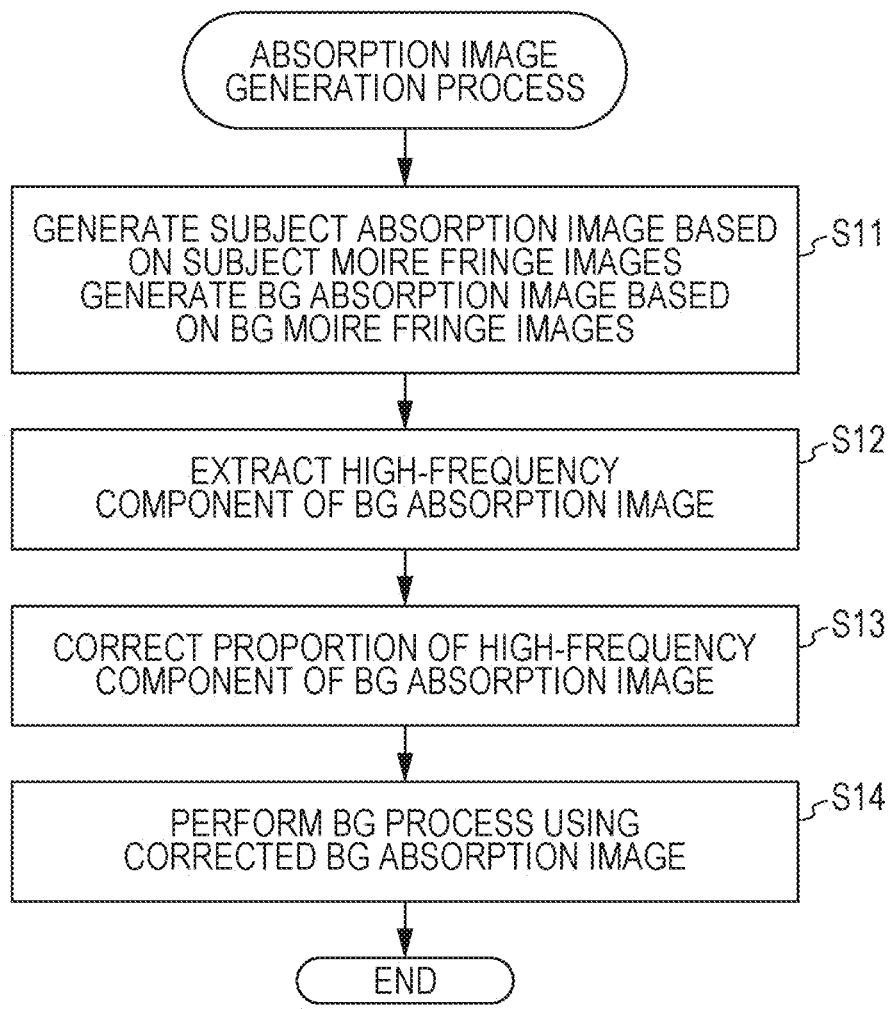

IMAGE PROCESSING SYSTEM AND IMAGE PROCESSING DEVICE

The entire disclosure of Japanese Patent Application No. 2015-036006 filed on Feb. 26, 2015 including description, claims, drawings, and abstract are incorporated herein by reference in its entirety.

BACKGROUND OF THE INVENTION

Field of the Invention

The present invention relates to a medical image system and an image processing device.

Description of the Related Art

X-ray equipment, such as Talbot interferometers and Talbot-Lau interferometers, that utilizes the Talbot effect has been known. The Talbot effect refers to a phenomenon of coherent light, which has passed through a first grating having slits formed at regular intervals, forming a lattice image of the first grating in regular cycles in the light traveling direction. The lattice image is called a self-image. A Talbot interferometer or a Talbot-Lau interferometer has a second grating disposed at a position where the self-image is formed, so as to measure interference fringes generated by slightly shifting the second grating. Since moires are distorted by an object placed before the second grating, in order to conduct radiographing using a Talbot interferometer or a Talbot-Lau interferometer, a subject may be placed before the first grating and irradiated with coherent X-rays, and the resulting moire fringe images may be computed so as to obtain a reconstructed image (an absorption image, a differential phase image, or a small-angle scattering image) of the subject.

Note that, if moire fringe images are radiographed with X-ray equipment having a Talbot interferometer or a Talbot-Lau interferometer as described above and the moire fringe images are simply reconstructed, image unevenness caused by a grating used therein is contained in the reconstructed image.

In order to attenuate the image unevenness, correction (hereinafter referred to as a BG process) is conducted in such a manner that a subject reconstructed image generated on the basis of subject moire fringe images acquired by radiographing a subject is subtracted or divided by a background reconstructed image (a BG reconstructed image) generated on the basis of background moire fringe images (hereinafter referred to as BG moire fringe images) acquired by radiographing without placing a subject (hereinafter referred to as background radiographing or BG radiographing.

Since, however, the X-ray spectra of X-rays passing through the subject change, image unevenness caused by the first grating or the second grating also remain in the corrected absorption image or small-angle scattering image resulting from the BG process.

Thus, JP 2014-135989 A, for example, discloses conducting BG radiographing with a homogeneous member that causes the same X-ray spectral change as that caused by X-rays passing through the subject, and performing the BG process by using a BG reconstructed image generated on the basis of the resulting BG moire fringe images, so as to reduce image unevenness remaining in the subject reconstructed image due to the change in the X-ray spectra.

With the technique of JP 2014-135989 A, however, BG radiographing needs to be conducted with a member causing an X-ray spectral change equivalent to that caused by the subject or such radiographing needs to be conducted in advance, which is more troublesome and complicated than the BG radiographing of the related art.

SUMMARY OF THE INVENTION

An object of the present invention is to enable reduction in image unevenness easily without the trouble of placing a member that causes an X-ray spectral change equivalent to that caused by the subject in BG radiographing.

To achieve the abovementioned object, according to an aspect, a medical image system reflecting one aspect of the present invention comprises: X-ray equipment having a Talbot interferometer or a Talbot-Lau interferometer, the X-ray equipment including: an X-ray source configured to emit X-rays; a plurality of gratings arranged in a emitting direction of the X-rays, each of the gratings having a plurality of slits arranged in a direction perpendicular to the emitting direction of the X-rays; and an X-ray detector irradiated by the X-ray source, the X-ray detector having conversion elements for accumulating charge according to X rays having passed through the gratings and generating electrical signals, the conversion elements being arranged two-dimensionally, the X-ray detector being configured to read the electrical signals generated by the conversion elements to acquire moire fringe image; a subject absorption image generation unit configured to generate a subject absorption image based on moire fringe images containing a subject that are acquired in such a manner that the subject is placed on a subject placement position provided on an emission path of the X-rays and X-rays are emitted from the X-ray source; a subjectless absorption image generation unit configured to generate a subjectless absorption image based on subjectless more fringe images acquired in such a manner that X-rays are emitted from the X-ray source with no subject placed at the subject placement position provided on the emission path of the X-rays; and an image unevenness correction unit configured to correct image unevenness of the subject absorption image by using the subjectless absorption image, the medical image system further comprising a subjectless absorption image correction unit configured to correct only a proportion of a high-frequency component in the subjectless absorption image, wherein the image unevenness correction unit corrects image unevenness of the subject absorption image by using the subjectless absorption image corrected by the subjectless absorption image correction unit.

In one aspect of the invention in Item. 2, according to Item. 1, the subjectless absorption image correction unit preferably extracts a high-frequency component in units of pixels of the subjectless absorption image, and corrects only a proportion of high-frequency component in the subjectless absorption image by multiplying the high-frequency component by a correction coefficient for correcting the high-frequency component to that of the subject absorption image.

In one aspect of the invention in Item. 3, according to Item. 2, the subjectless absorption image correction unit preferably sets a correction coefficient according to a value of each pixel of an image obtained by correcting the subject absorption image by using the subjectless absorption image before being corrected for a corresponding pixel in the subjectless absorption image.

In one aspect of the invention in Item. 4, according to Item. 2 or 3, the subjectless absorption image correction unit preferably sets different correction coefficients between an area corresponding to a bone part area and an area corresponding to a soft part area in the subject absorption image.

In one aspect of the invention in Item. 5, according to any one of Items. 2 to 4, the subjectless absorption image correction unit preferably sets a correction coefficient according to a value of a high-frequency component of each of pixels in the subjectless absorption image for the pixel.

In one aspect of the invention in Item. 6, according to any one of Items. 1 to 5, the image unevenness correction unit preferably corrects image unevenness of the subject absorption image by dividing the subject absorption image by the corrected subjectless absorption image.

To achieve the abovementioned object, according to an aspect, an image processing device for performing image processing on an image acquired by X-ray equipment having a Talbot interferometer or a Talbot-Lau interferometer reflecting one aspect of the present invention comprises: a subject absorption image generation unit configured to generate a subject absorption image based on moire fringe images containing a subject that are acquired in such a manner that the subject is placed on a subject placement position provided on an emission path of X-rays in the X-ray equipment and X-rays are emitted; a subjectless absorption image generation unit configured to generate a subjectless absorption image based on subjectless moire fringe images acquired in such a manner that X-rays are emitted with no subject placed at the subject placement position provided on the emission path of the X-rays in the X-ray equipment; a subjectless absorption image correction unit configured to correct only a proportion of a high-frequency component in the subjectless absorption image; and an image unevenness correction unit configured to correct image unevenness of the subject absorption image by using the subjectless absorption image corrected by the subjectless absorption image correction unit.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 11 is a flowchart of an absorption image generation process performed by a control unit in FIG. 4;

DESCRIPTION OF THE PREFERRED EMBODIMENTS

Hereinafter, an embodiment of the present invention will be described with reference to the drawings. However, the scope of the invention is not limited to the illustrated examples.

Figure 1:
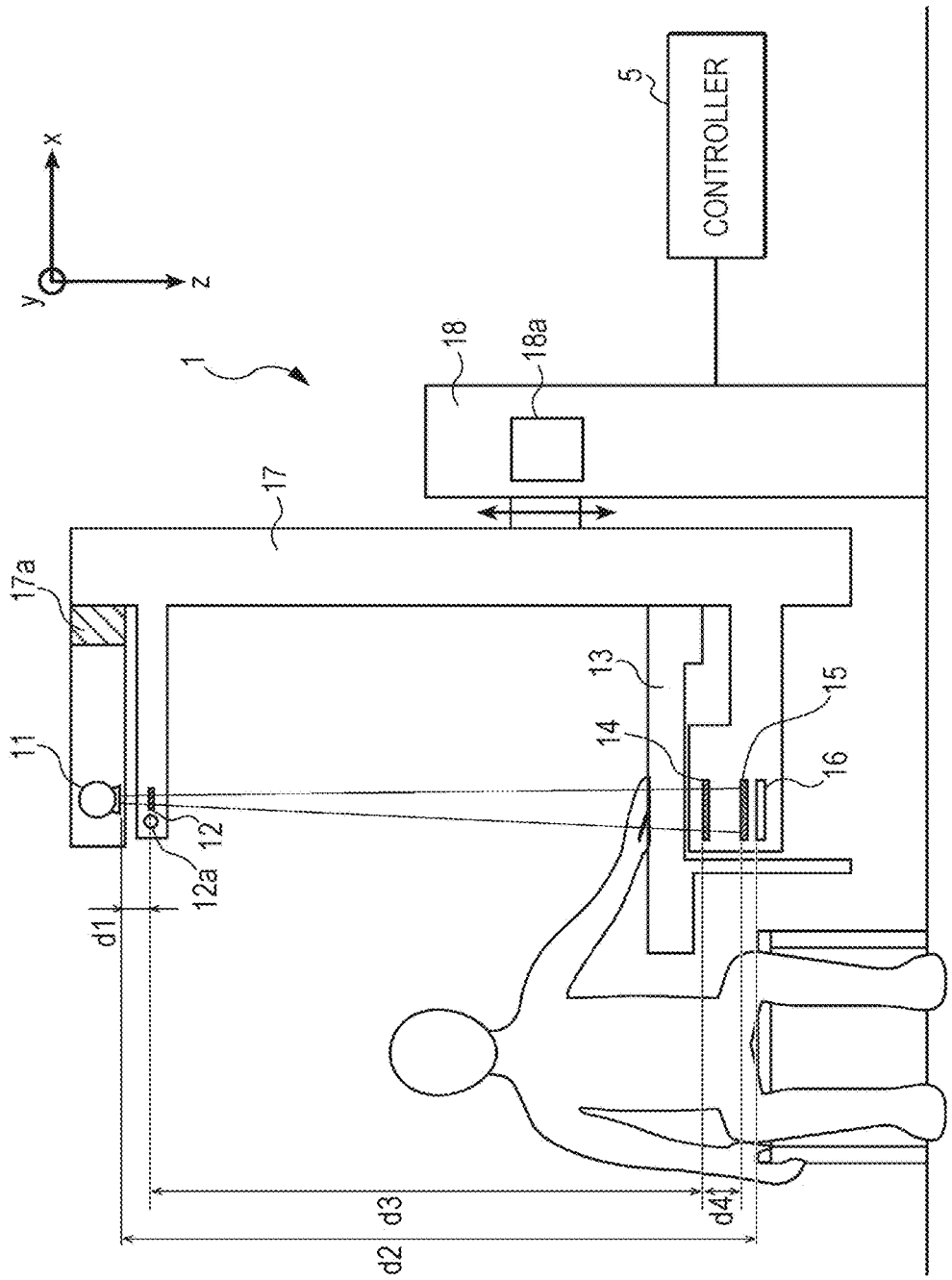
FIG. 1 is a diagram showing an overall configuration of a medical image system according to an embodiment.

FIG. 1 illustrates a medical image system according to the embodiment of the present invention. The medical image system includes X-ray equipment 1 and a controller 5. The X-ray equipment 1 takes X-rays with a Talbot-Lau interferometer, and the controller 5 generates a reconstructed image of a subject by using a plurality of moire fringe images obtained by the radiography.

As shown in FIG. 1, the X-ray equipment 1 includes an X-ray source 11, a multislit 12, a subject table 13, a first grating 14, a second grating 15, an X-ray detector 16, a holding unit 17, and a main unit 18, among others.

The X-ray equipment 1 of a vertical type, in which the X-ray source 11, the multislit 12, the subject table 13, the first grating 14, the second grating 15, and X-ray detector 16 are disposed in this order along a z direction that is the direction of the gravitational force. The distance between the focal spot of the X-ray source 11 and the multislit 12 is represented by d1 (mm), the distance between the focal spot of the X-ray source 11 and the X-ray detector 16 is represented by d2 (mm), the distance between the multislit 12 and the first grating 14 is represented by d3 (mm), and the distance between the first grating 14 and the second grating 15 is represented by d4 (mm). Note that the position of the subject table 13 may alternatively be between the first grating 14 and the second grating 15.

The distance d1 is preferably in a range of 5 to 500 (mm), and more preferably in a range of 5 to 300 (mm).

The distance d2 is preferably at least equal to or smaller than 3000 (mm) because the height of a X-ray room is typically about 3 (m) or lower. In particular, the distance d2 is preferably in a range of 400 to 3000 (mm), and more preferably in a range of 500 to 2000 (mm).

The distance (d1+d3) between the focal spot of the X-ray source 11 and the first grating 14 is preferably in a range of 300 to 3000 (mm), and more preferably in a range of 400 to 1800 (mm).

The distance (d1+d3+d4) between the focal spot of the X-ray source 11 and the second grating 15 is preferably in a range of 400 to 3000 (mm), and more preferably in a range of 500 to 2000 (mm).

The respective distances may be set in such a manner that optimum distances with which a lattice image (self-image) of the first grating 14 is superposed on the second grating 15 are calculated from the wavelength of X-rays emitted by the X-ray source 11.

The X-ray source 11, the multislit 12, the subject table 13, the first grating 14, the second grating 15, and the X-ray detector 16 are integrally held by one holding unit 17, so that the relative positions thereof in the z direction are fixed. The holding unit 17 is formed in an arm shape, and attached to the main unit 18 in such a manner that the holding unit 17 can be moved in the z direction by a drive unit 18a disposed in the main unit 18.

The X-ray source 11 is held with a buffer member 17a between the X ray source 11 and the holding unit 17. The buffer member 17a may be any material capable of absorbing shock and oscillation, and an example thereof is an elastomer. Since the X-ray source 11 generates heat caused by X-ray emission, it is preferable that the buffer member 17a on the side of the X-ray source 11 be further made of a heat insulating material.

The X-ray source 11 includes an X-ray tube, generates X-rays with the X-ray tube and emits the X-rays in the direction of the gravitational force (z direction). Examples of the X-ray tube that may be used include the Coolidge X-ray tube and the rotating anode X-ray tube, which are generally used widely in medical practice. For the anode, tungsten or molybdenum may be used.

The focal spot diameter of the X-rays is preferably in a range of 0.03 to 3 (mm), and more preferably in a range of 0.1 to 1 (mm).

An irradiation field stop, which is not shown, for narrowing the X-ray irradiation range is provided in the X-ray emitting direction of the X-ray source 11.

Figure 2:
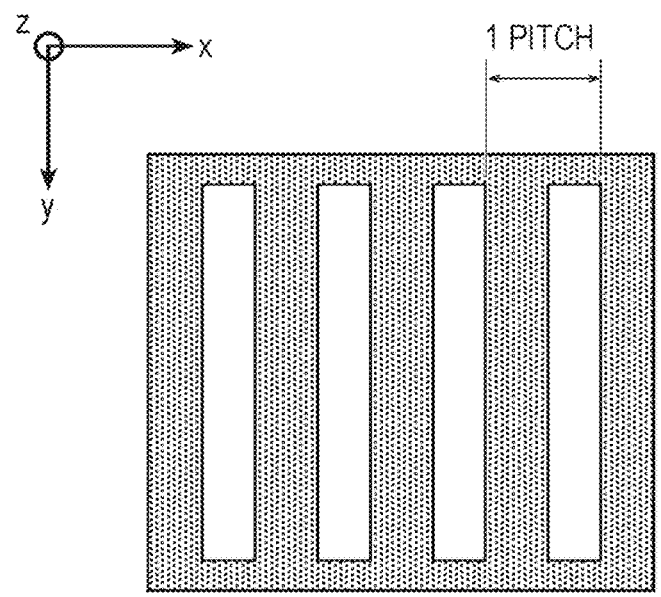
FIG. 2 is a plan view of a multislit.

The multislit 12 (third grating) is a diffraction grating, and has a plurality of slits arranged at predetermined intervals in an x direction as shown in FIG. 2. The multislit 12 is formed of a material having a high X-ray shielding property, that is, a high X-ray absorption property, such as tungsten, lead, or gold, on a substrate of a material having a low X-ray absorption property such as silicon or glass. For example, photolithography is used to mask a resist layer in a pattern of the slits and irradiate the resist layer with ultraviolet, so that the slit pattern is transferred onto the resist layer. Slit structures having the same shape as the pattern are obtained through exposure, a space between the slit structures is filled with metal by electroforming, and the multislit 12 is thus formed.

The multislit 12 has a slit pitch in a range of 1 to 60 (μm). One slit pitch refers to the distance between adjacent slits as shown in FIG. 2. The slit width (length in the x direction) thereof is a length in a range of 1 to 60(%) of the slit pitch, and more preferably in a range of 10 to 40(%) thereof. The slit height (length in the z direction) thereof is in a range of 1 to 500 (μm), and preferably in a range of 1 to 150 (μm).

When the slit pitch of the multislit 12 is represented by $w_0$ (μm) and the slit pitch of the first grating 14 is represented by $w_1$ (μm), the slit pitch $w_0$ can be obtained by the following expression:

$$w_0 = w_1 \cdot (d3+d4)/d4$$

When the pitch $w_0$ is determined to satisfy the expression, self-images formed by X-rays having passed through the slits of the multislit 12 and those of the first grating 14 overlap each other on the second grating 15, and come into what is called an in-focus state.

As shown in FIG. 1, a drive unit 12a for moving the multislit 12 in the x direction perpendicular to the z direction is provided adjacent to the multislit 12. For the drive unit 12a, a drive mechanism having a relatively large reduction ratio such as a worm reducer, for example, can be used alone or in combination.

The subject table 13 is a table for placing a subject thereon being disposed at a subject placement position on a X-ray irradiation path from the X-ray source 11.

The first grating 14 is a diffraction grating having a plurality of slits arranged at predetermined intervals in the x direction similarly to the multislit 12 (see FIG. 2). The first grating 14 may be formed by using ultraviolet similarly to the multislit 12, or may be a grid structure formed only of silicon by deep etching on a silicon substrate using a so-called ICP method. The first grating 14 has a slit pitch in a range of 1 to 20 (μm). The slit width thereof is in a range of 20 to 70(%) of the slit pitch, and preferably in a range of 35 to 60(%) thereof. The slit height thereof is in a range of 1 to 100 (μm).

When a phase grating is used as the first grating 14, the slit height is a height at which the phase difference of two materials constituting a slit pitch, that is, the materials of an X-ray transmitting part and an X-ray shielding part is in a range of π/8 to 15×π/8. The slit height is preferably a height at which the phase difference is π/2 or π. When an absorption grating is used as the first grating 14, the slit height thereof is a height at which X-rays are sufficiently absorbed by the X-ray shielding part.

When the first grating 14 is a phase grating where the phase difference of the materials of the X-ray transmitting part and the X-ray shielding part is π/2, the distance d4 between the first grating 14 and the second grating 15 needs to substantially satisfy the following condition:

$$d4 = (m+\tfrac{1}{2}) \cdot w_1^2 / \lambda$$

In the expression, m is an integer, and λ represents the wavelength of an X-ray.

The second grating 15 is a diffraction grating having a plurality of slits arranged at predetermined intervals in the x direction similarly to the multislit 12 (see FIG. 2). The second grating 15 can also be formed by photolithography. The second grating 15 has a slit pitch in a range of 1 to 20 (μm). The slit width thereof is in a range of 30 to 70(%) of the slit pitch, and preferably 35 to 60(%) thereof. The slit height thereof is in a range of 1 to 100 (μm).

While the first grating 14 and the second grating 15 have grating surfaces that are perpendicular to the z direction (within and parallel to the x-y plane) and have slits in directions tilted with respect to each other at a predetermined angle (slightly) within the x-y plane in the present embodiment, the first grating 14 and the second grating 15 may alternatively be parallel to each other.

The multislit 12, the first grating 14, and the second grating 15 can have the following features, for example:

Focal spot diameter of the X-ray source 11: 300 (μm), tube voltage: 40 (kVp), added filter: aluminum 1.6 (mm);

Distance d1 from the focal spot of the X-ray source 11 to the multislit 12: 240 (mm);

Distance d3 from the multislit 12 to the first grating 14: 1110 (mm);

Distance d3+d4 from the multislit 12 to the second grating 15: 1370 (mm);

Size of the multislit: 12 (square mm), slit pitch thereof: 22.8 (μm);

Size of the first grating 14: 50 (square mm), slit pitch thereof: 4.3 (μm); and

Size of the second grating 15: 50 (square mm), slit pitch thereof: 5.3 (μm).

The X-ray detector 16 has multiple conversion elements configured to generate electrical signals according to emitted X-rays and arranged two-dimensionally, and reads the electrical signals generated by the conversion elements as image signals.

The X-ray detector 16 has a pixel size in a range of 10 to 300 (μm), and more preferably in a range of 50 to 200 (μm).

The X-ray detector 16 is preferably fixed to the holding unit 17 at a position in contact with the second grating 15. This is because moire fringe images obtained by the X-ray detector 16 are more blurred as the distance between the second grating 15 and the X-ray detector 16 is larger.

For the X-ray detector 16, a flat panel detector (FPD) may be used. The FPD may be either of an indirect conversion FPD configured to convert detected X-rays into electrical signals through photoelectric conversion elements or a direct conversion FPD configured to convert detected X-rays directly into electrical signals.

The indirect conversion FPD includes photoelectric conversion elements arranged two-dimensionally with thin film transistors (TFTs) under a scintillator plate of CsI, $Gd_2O_2S$, or the like and each constituting a pixel. When X-rays having entered the X-ray detector 16 are absorbed by the scintillator plate, the scintillator plate emits light. The emitted light causes charge to be accumulated in the photoelectric conversion elements, and the accumulated charge is read as image signals.

In the direct conversion FPD, an amorphous selenium film having a thickness in a range of 100 to 1000 (μm) is formed on a glass and the amorphous selenium and electrodes are deposited on an array of two-dimensionally arranged TFTs by thermal deposition of amorphous selenium. When the amorphous selenium film absorbs X-rays, electrons are liberated in the substance in the form of electron-hole pairs, and voltage signals between electrodes are read by the TFTs.

Alternatively, an imaging means such as a charge coupled device (CCD) or an X-ray camera may be used as the X-ray detector 16.

Figure 3:
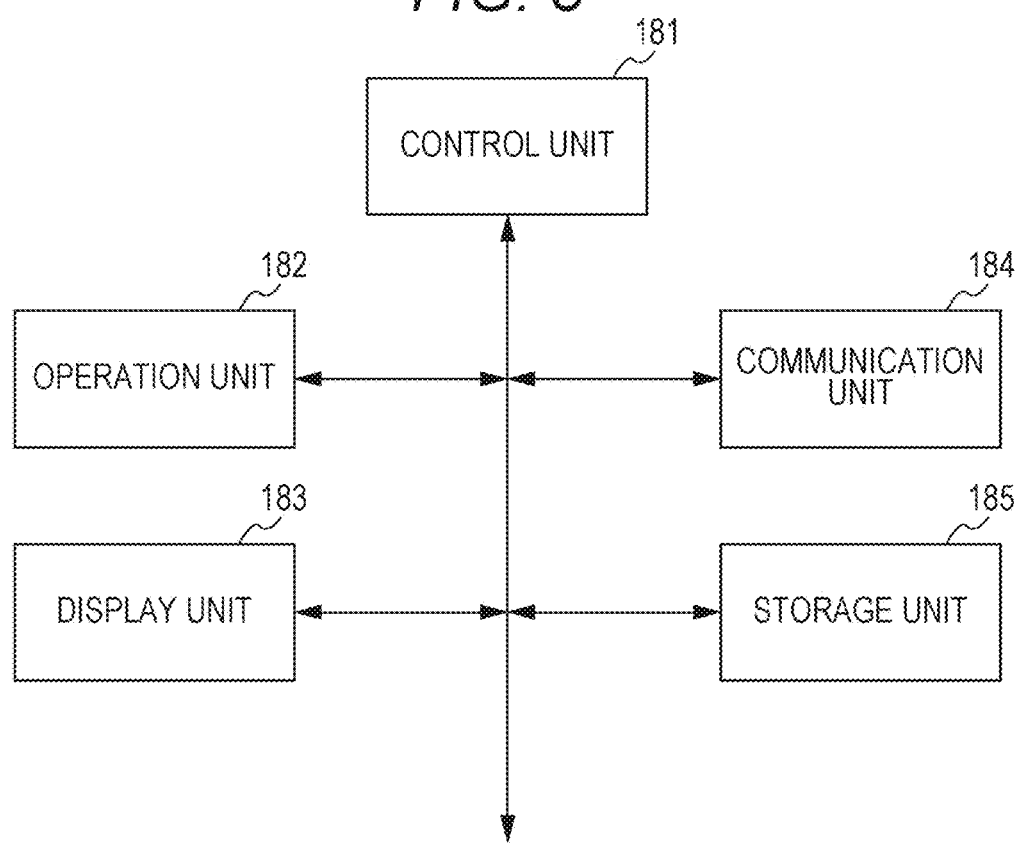
FIG. 3 is a block diagram showing a functional configuration of a main unit in FIG. 1.

As shown in FIG. 3, the main unit 18 includes a control unit 181, an operation unit 182, a display unit 183, a communication unit 184, a storage unit 185, etc.

The control unit 181 includes a central processing unit (CPU), a random access memory (RAM), and the like, and executes various processes in cooperation with programs stored in the storage unit 185. The control unit 181 is connected to such components as the X-ray source 11, the drive unit 12a, the drive unit 18a, and the X-ray detector 16, and executes radiographing control processes and the like, which will be described later, to control the timing of irradiation with X-rays from the X-ray source 11, X-ray irradiation conditions, the timing of reading image signals by the X-ray detector 16, shifting of the multislit 12, etc., according to setting information on radiographing conditions input from the controller 5, for example.

The operation unit 182 includes an exposure switch and the like, and is configured to generate an operation signal according to operation of such components and output the operation signal to the control unit 181.

The display unit 183 displays operation screens, an operation status of the X-ray equipment 1, etc. on a display according to display control of the control unit 181.

The communication unit 184 includes a communication interface, and communicates with the controller 5 in a network. For example, the communication unit 184 transmits moire fringe images read by the X-ray detector 16 and stored in the storage unit 185 to the controller 5.

The storage unit 185 stores programs to be executed by the control unit 181 and data necessary for execution of the programs. The storage unit 185 also stores moire fringe images obtained by the X-ray detector 16.

The controller 5 controls radiographing operation of the X-ray equipment 1 according to operation performed by an operator. The controller 5 also serves as an image processing device that performs image processing on a series of moire fringe images obtained by the X-ray equipment 1. For example, the controller 5 generates a reconstructed image (an absorption image, a small-angle scattering image, or a differential phase image) of a subject by using a series of moire fringe images obtained by the X-ray equipment 1.

Figure 4:
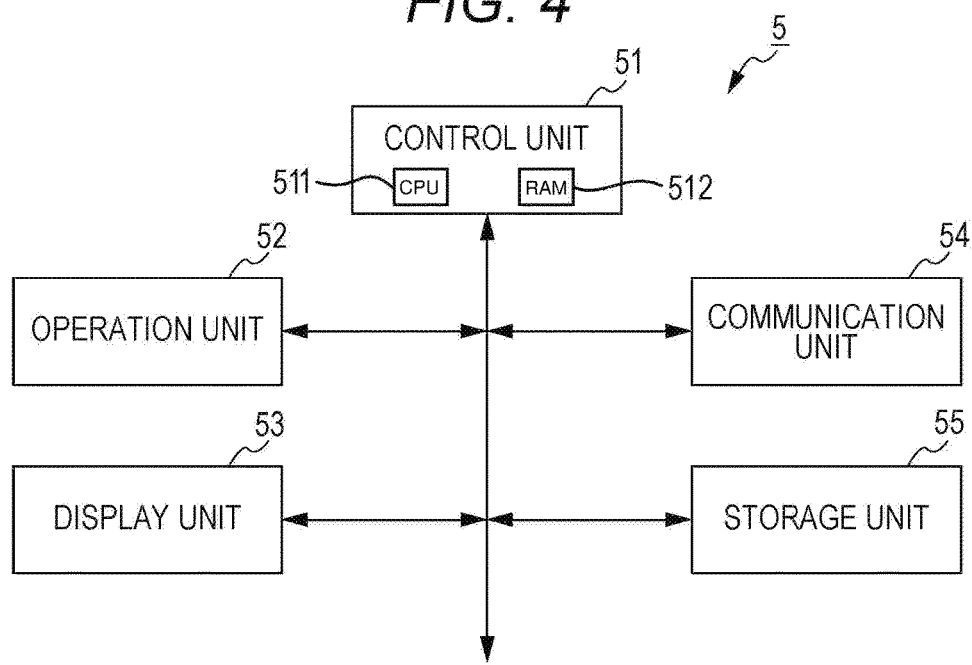
FIG. 4 is a block diagram showing a functional configuration of a controller in FIG. 1.

As shown in FIG. 4, the controller 5 includes a control unit 51, an operation unit 52, a display unit 53, a communication unit 54, and a storage unit 55.

The control unit 51 includes a central processing unit (CPU) 511, a random access memory (RAM) 512, and the like, and executes various processes including an absorption image generation process, which will be described later, in cooperation with programs stored in the storage unit 55. The control unit 51 functions as a subject absorption image generation unit, a subjectless absorption image generation unit, a subjectless absorption image correction unit, and an image unevenness correction unit.

The operation unit 52 includes a keyboard having cursor keys, numeric keys, various function keys, etc. and a pointing device such as a mouse, and is configured to output press signals of pressed keys on the keyboard and operation signals input by the mouse as input signals to the control unit 51. The operation unit 52 may alternatively have a touch panel integrated with the display of the display unit 53, and be configured to generate operation signals according to operation of such components and output the operation signals to the control unit 51.

The display unit 53 includes a monitor of a cathode ray tube (CRT), a liquid crystal display (LCD), or the like, and displays operation screens, generated reconstructed images, etc. according to display control of the control unit 51.

The communication unit 54 includes a communication interface, and communicates with the X-ray equipment 1 and the X-ray detector 16 in a network in a wired or wireless manner. For example, the communication unit 54 transmits radiographing conditions and control signals to the X-ray equipment 1, and receives moire fringe images from the X-ray equipment 1 or the X-ray detector 16.

The storage unit 55 stores programs to be executed by the control unit 51 and data necessary for execution of the programs. For example, the storage unit 55 stores radiographing order information that is information on radiographing reserved using a radiology information system (RIS), a hospital information system (HIS), or the like, which is not shown. The radiographing order information includes patient information such as patient IDs and patient names, radiographed part (subject part) information, etc.

The storage unit 55 also stores a radiographing condition table in which a subject part and radiographing conditions suitable for the subject part are associated with each other.

The storage unit 55 also stores moire fringe images obtained by the X-ray equipment 1 on the basis of the radiographing order information and a reconstructed image or the like generated on the basis of the moire fringe images in association with the radiographing order information.

The storage unit 55 also prestores gain correction data, a defective pixel map, and the like associated with the X-ray detector 16. The defective pixel map is position information (coordinates) of defective pixels (including no pixel) of the X-ray detector 16.

<Operation of Medical Image System>

Here, a radiography method using the Talbot-Lau interferometer of the X-ray equipment 1 will be described.

Figure 5:
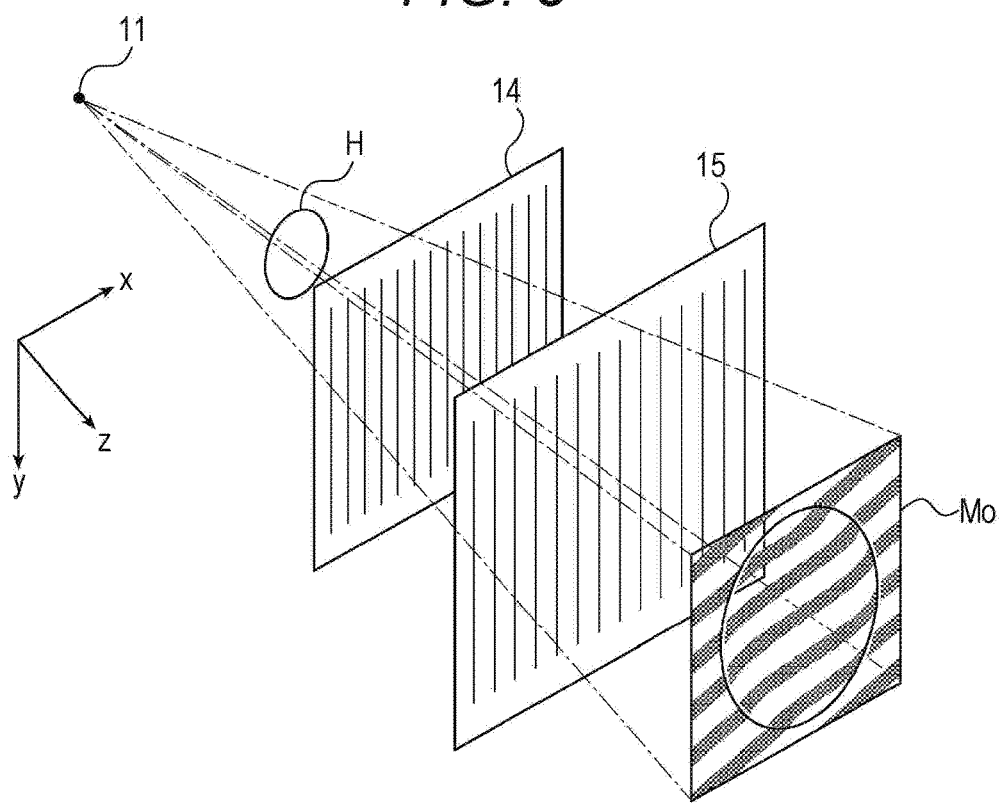
FIG. 5 is a diagram explaining the principle of a Talbot interferometer.

As shown in FIG. 5, when X-rays emitted by the X-ray source 11 passes through the first grating 14, the X-rays that have passed through the first grating 14 form images at regular intervals in the z direction. The images are called self-images, and the phenomenon of forming a self-image is called a Talbot effect. The second grating 15 is disposed at a position where a self-image is formed substantially in parallel with the self-image, and a moire fringe image (represented by Mo in FIG. 5) is obtained from X-rays having passed through the second grating 15. Specifically, the first grating 14 forms a periodic pattern, and the second grating 15 converts the periodic pattern to moire fringes. When a subject (represented by H in FIG. 5) is present between the X-ray source 11 and the first grating 14, the subject causes the phases of X-rays to be shifted, and the moire fringes in the moire fringe image are thus distorted within the edge of the subject as shown in FIG. 5. This distortion of the moire fringes is detected by processing the moire fringe image, and the subject image can thus be formed. This is the principle of a Talbot interferometer.

In the X-ray equipment 1, the multislit 12 is disposed at a position close to the X-ray source 11 between the X-ray source 11 and the first grating 14, and radiography is conducted by the Talbot-Lau interferometer. Although a Talbot interferometer operates on the condition that the X-ray source 11 is an ideal point source, a focal spot having a relatively large focal spot diameter is used in actual radiography. The multislit 12 is thus used so as to generate multiple X-ray source functioning as if multiple point sources emit X-rays. This is the radiography method conducted by the Talbot-Lau interferometer, which can produce the Talbot effect similarly to the Talbot interferometer even when the focal spot diameter is relatively large.

In the present embodiment, radiography is conducted according to a fringe scanning method. Fringe scanning generally refers to conducting M times (M is a positive integer where M>2) of radiography (M-step radiographing) while relatively shifting any one (the multislit 12 in the present embodiment) of the gratings (the multislit 12, the first grating 14, and the second grating 15) in the slit pitch direction (x direction) to acquire M moire fringe images required for generating one reconstructed image. Specifically, when the slit pitch of the grating to be shifted is represented by d (μm), shifting the grating by d/M (μm) in the slit pitch direction and conducting radiographing are repeated, so that M moire fringe images are acquired.

In a Talbot-Lau interferometer of the related art, a multislit 12 is used for generating a multiple X-ray source and increasing the X-ray emission amount as mentioned above, and a first grating 14 or a second grating 15 is relatively shifted so that multiple moire fringe images are acquired by the fringe scanning method. In the present embodiment, however, the multislit 12 is shifted relative to the first grating 14 and the second grating 15 while the positions of the first grating 14 and the second grating 15 are fixed instead of relatively shifting the first grating 14 or the second grating 15, so that multiple moire fringe images at regular intervals are acquired.

Figure 6:
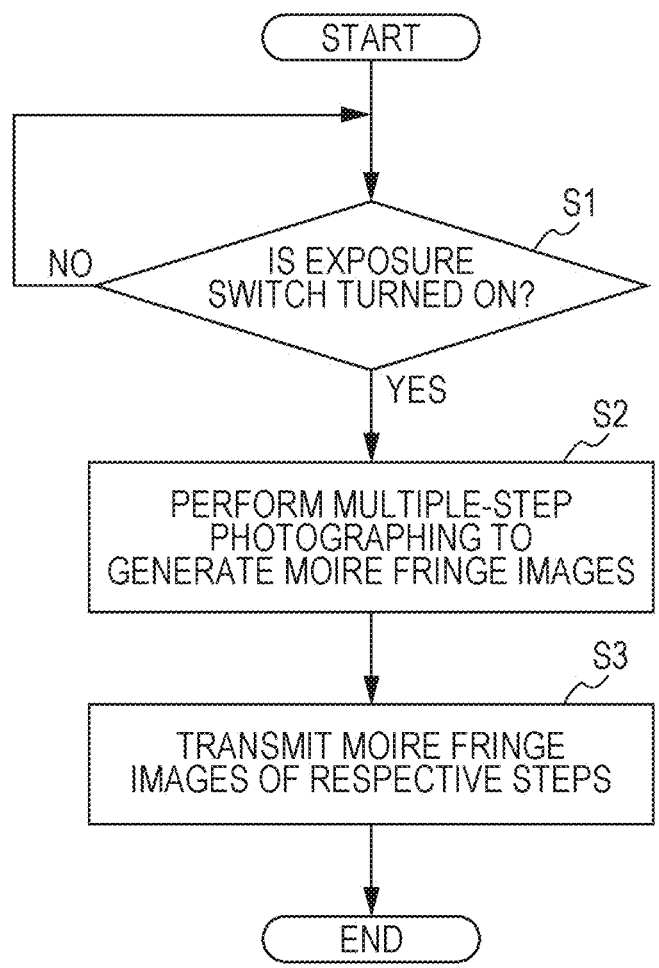
FIG. 6 is a flowchart showing a radiography control process performed by a control unit in FIG. 3.

FIG. 6 is a flowchart showing the radiography control process performed by the control unit 181 of the X-ray equipment 1. A flow of the radiography control process will be described with reference to FIG. 6.

First, when the exposure switch of the operation unit 182 is operated by an operator (step S1; YES), the control unit 181 controls the X-ray source 11, the X-ray detector 16, and the drive unit 12*a* to sequentially perform multiple-step radiographing and acquire a series of moire fringe images with moire fringes having different phases (step S2).

In the sequential radiographing, emission of X-rays by the X-ray source 11 is first started with the multislit 12 in a stopped state. In the X-ray detector 16, resetting is performed to remove unnecessary charge remaining after previous radiographing, charge is then accumulated according to the timing of X-ray emission, and the accumulated charge is read as image signals according to the timing of stopping the X-ray emission. This corresponds to one step of radiographing. Shifting of the multislit 12 is started at a timing when one step of radiographing ends, the multislit 12 is stopped after being shifted for a predetermined distance, and radiographing of the next step is conducted. In this manner, shifting and stopping of the multislit 12 are repeated the number of times corresponding a predetermined number of steps, and X-ray emission and reading of image signals are conducted each time the multislit 12 is stopped. The sequential radiographing for acquiring multiple moire fringe images required for generating one reconstructed image ends when radiographing with the multislit 12 shifted by one slit pitch is terminated.

The number M of steps in the sequential radiographing is in a range of 2 to 20, and more preferably in a range of 3 to 10. The number of steps is preferably five in view of acquiring a reconstructed image being high in visibility in a short time (Reference 1: K. Hibino, B. F. Oreb and D. I. Farrant, Phase shifting for nonsinusoidal wave forms with phase-shift errors, J. Opt. Soc. Am. A, Vol. 12, 761-768 (1995); Reference 2: A. Momose, W. Yashiro, Y. Takeda, Y. Suzuki and T. Hattori, Phase Tomography by X-ray Talbot Interferometetry for biological imaging, Jpn. J. Appl. Phys., Vol. 45, 5254-5262 (2006)). Herein, description will be given on the assumption that five-step radiographing is performed.

Figure 7:
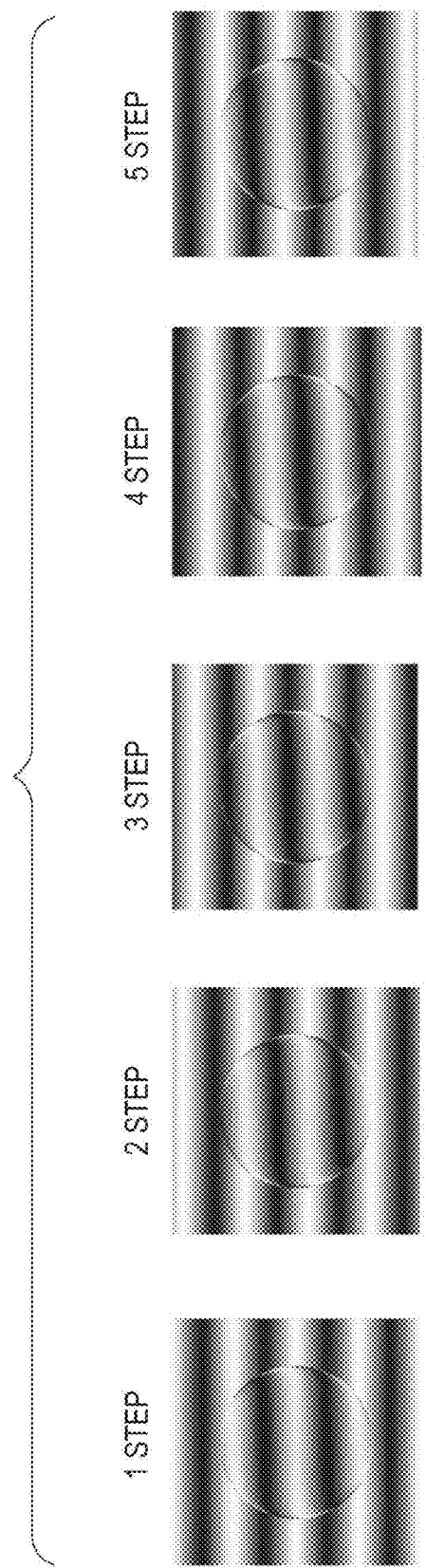
FIG. 7 shows moire fringe images acquired by five-step radiographing.

Assume, for example, that the multislit 12 has a slit pitch of 22.8 (μm) and that five-step radiographing is to be performed in ten seconds. Radiographing is conducted each time the multislit 12 is shifted by 4.56 (μm) corresponding to ⅕ of the slit pitch and then stopped. In terms of the radiographing time, radiographing is conducted at 2, 4, 6, 8, and 10 seconds after the exposure switch is turned on. If the multislit 12 can be shifted by a constant shifting amount with ideal shifting accuracy, five moire fringe images corresponding to one slit pitch of the multislit 12 are acquired by five-step radiographing as shown in FIG. 7.

After the sequential steps of radiographing is completed, the control unit 181 causes the communication unit 184 to transmit the moire fringe images of the respective steps to the controller 5 (step S3). One moire fringe image may be transmitted from the communication unit 184 to the controller 5 after each step of radiographing is completed, or all the moire fringe images may be transmitted at the same time after all the steps of radiographing are completed and all the moire fringe images are acquired.

In the present embodiment, radiographing with a subject placed on the subject table 13 (subject radiographing) and BG radiographing with no subject on the subject table 13 are conducted, so that subject moire fringe images (moire fringe images with a subject) and BG moire fringe images (subjectless moire fringe images) are acquired.

In the controller 5, when a series of subject moire fringe images and a series of BG moire fringe images from the main unit 18 are received by the communication unit 54, the control unit 51 generates a reconstructed image such as an absorption image, a differential phase image, or a small-angle scattering image on the basis of the received subject moire fringe images and BG moire fringe images.

Among reconstructed images, an absorption image $I_{AB}(x,y)$ is typically generated according to the following [Expression 1] (Reference 3: A. Momose, W. Yashiro, H. Kuwabara and K. Kawabata, Grating-Based X-ray Phase Imaging Using Multiline X-ray Source, Jpn. J. Appl. Phys., Vol. 48, 076512 (2009)):

[Formula 1]

$$I_{AB}(x, y) = \frac{I_{AB\_SAMPLE}(x, y)}{I_{AB\_BG}(x, y)} \quad \text{[Expression 1]}$$

where

[Formula 2]

$$I_{AB\_SAMPLE}(x, y) = \sum_{k=0}^{M-1} I_k^{SAMPLE}(x, y) \quad \text{[Expression 2]}$$

[Formula 3]

$$I_{AB\_BG}(x, y) = \sum_{k=0}^{M-1} I_k^{BG}(x, y) \quad \text{[Expression 3]}$$

$I_k^{SAMPLE}(x,y)$ and $I_k^{BG}(x,y)$ represent pixel values of a subject moire fringe image and a BG moire fringe image, respectively, at the k-th radiographing. (x,y) represents two-dimensional coordinates of a pixel in each image. $I_{AB\_SAMPLE}(x,y)$ and $I_{AB\_BG}(x,y)$ represent pixel values of a subject absorption image and a BG absorption image (subjectless absorption image), respectively.

Figure 8:
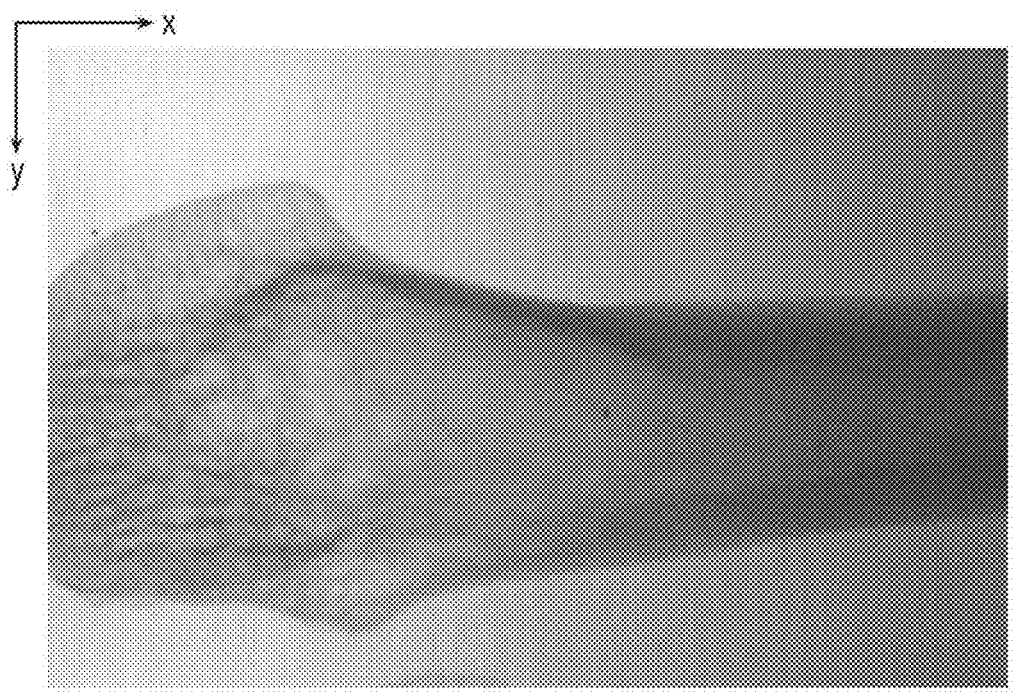
FIG. 8 is a subject absorption image acquired by radiographing a phantom as a subject with a Talbot-Lau interferometer.
Figure 9:
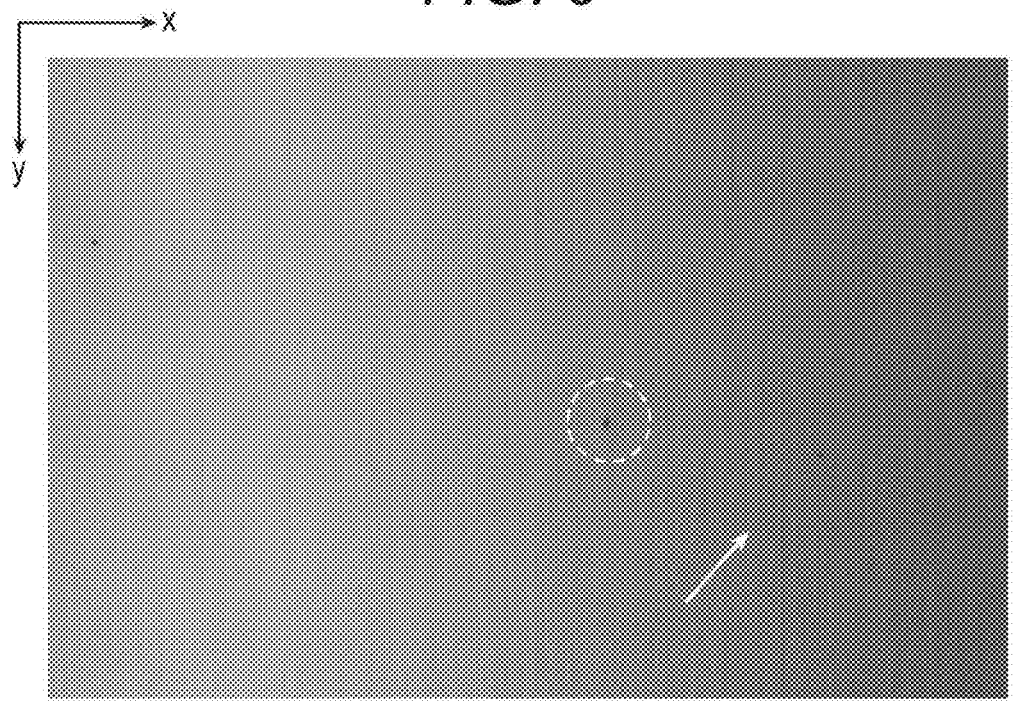
FIG. 9 is a BG absorption image acquired by radiographing with no phantom being placed under the same radiographing conditions as those in FIG. 8.

FIG. 8 shows an example of a subject absorption image $I_{AB\_SAMPLE}(x,y)$ acquired by radiographing a phantom with a tungsten tube and a Talbot-Lau interferometer of 40 kVp (added filter: aluminum 2.3 mm). FIG. 9 shows an example of a BG absorption image $I_{AB\_BG}(x,y)$ acquired by radiographing without a phantom under the same radiographing conditions as those in FIG. 8. Note that arrows and broken lines shown in FIG. 9 and subsequent drawings indicate image unevenness. In the images of FIGS. 8 and 9, fine stripes in the vertical direction of the drawing sheets are considered to be image unevenness mainly caused by unevenness in height and pitch of the grating generating in fabrication of the second grating 15.

The image unevenness caused by the grating should appear similarly in the subject absorption image $I_{AB\_SAMPLE}(x,y)$ and the BG absorption image $I_{AB\_BG}(x,y)$, and an absorption image $I_{AB}(x,y)$ indicating attenuation of X-rays due to the subject and not being affected by the unevenness caused by the grating should be obtained on the basis of a ratio of the subject absorption image $I_{AB\_SAMPLE}(x,y)$ and the BG absorption image $I_{AB\_BG}(x,y)$. In practice, however, it is found that image unevenness due to the grating remains in the absorption image $I_{AB}(x,y)$ generated on the basis of a ratio of the subject absorption image $I_{AB\_SAMPLE}(x,y)$ and the BG absorption image $I_{AB\_BG}(x,y)$.

Figure 10A:
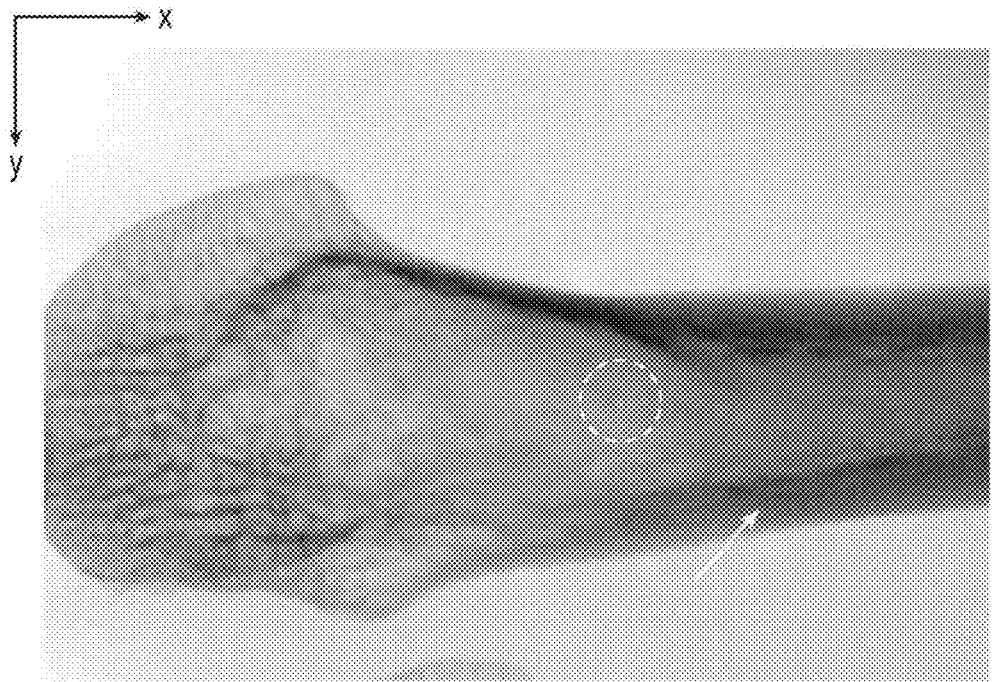
FIG. 10A is an image obtained by taking a natural logarithm of an absorption image $I_{AB}$ obtained by dividing the subject absorption image of FIG. 8 by the BG absorption image of FIG. 9.

FIG. 10A is an image obtained by taking the natural logarithm of an absorption image $I_{AB}(x,y)$ obtained by dividing the subject absorption image $I_{AB\_SAMPLE}(x,y)$ of FIG. 8 by the BG absorption image $I_{AB\_BG}(x,y)$ of FIG. 9 according to [Expression 1]. Furthermore, FIG. 10B is an image for visualizing the image unevenness remaining in the image of FIG. 10A more clearly, which is a differential absorption image calculated by subtracting pixel values of pixels adjacent to both sides of each of the pixels in the x direction (left-right direction on the drawing sheet) of the image of FIG. 10A.

Figure 10B:
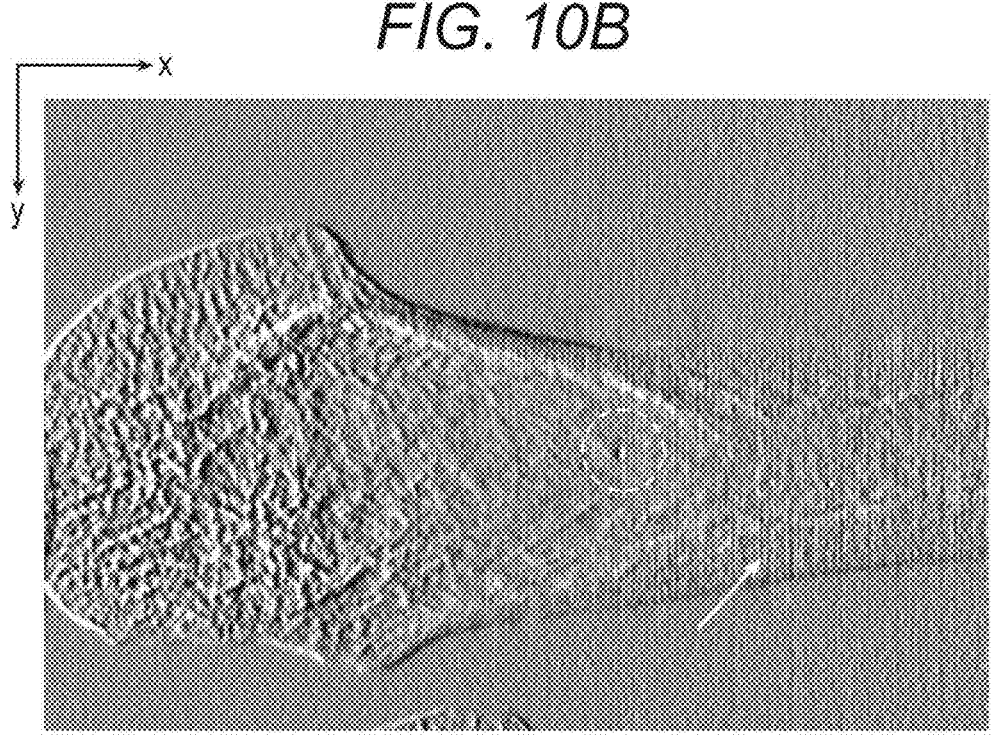
FIG. 10B is a differential absorption image of the image of FIG. 10A.

In the images shown in FIGS. 10A and 10B, it can be seen that the unevenness in vertical stripes (indicated by arrows in FIGS. 9 and 10A) and particle-like unevenness (regions in broken circles in FIGS. 9 and 10A) seen in the images of FIGS. 8 and 9 remain. These are image unevenness seen in both of the subject absorption image $I_{AB\_SAMPLE}(x,y)$ and the BG absorption image $I_{AB\_BG}(x,y)$, but the proportion of the unevenness to pixel values is different between the subject absorption image $I_{AB\_SAMPLE}(x,y)$ and the BG absorption image $I_{AB\_BG}(x,y)$. Thus, these are deemed to remain as image unevenness in the absorption image $I_{AB}(x,y)$ resulting from BG processing. The reason why the proportion of the unevenness to the pixel values is different between the subject absorption image $I_{AB\_SAMPLE}(x,y)$ and the BG absorption image $I_{AB\_BG}(x,y)$ is that low-energy X-rays are absorbed while X rays pass through the subject, resulting in a change in the X-ray spectral distribution in which high-energy X-rays increase. Typically, unevenness is less likely to be caused as X-rays have higher energy. In other words, the proportion of unevenness to the pixel values is higher in the subject absorption image $I_{AB\_SAMPLE}(x,y)$ than in the BG absorption image $I_{AB\_BG}(x,y)$.

The inventors of the present application have therefore found that the image unevenness seen in FIGS. 10A and 10B can be reduced (removed) by extracting a high-frequency component corresponding to the image unevenness from the BG absorption image $I_{AB\_BG}(x,y)$, and carrying out correction by multiplying the extracted high-frequency component by a correction coefficient a(x,y) (hereinafter referred to as a coefficient a(x,y); a≤1) to reduce the proportion of the high-frequency component according to the subject absorption image $I_{AB\_SAMPLE}(x,y)$.

Note that, in JP 2014-135989 A, it is assumed that radiographing is performed with a member causing X-ray spectral variation equivalent to that of the subject is placed in BG radiographing, so that the image unevenness is reduced (attenuated). In this case, since the amount of X-rays reaching the X-ray detector is decreased by an amount corresponding to the placement of the member, the pixel values of the entire BG absorption image are lowered, and noise disadvantageously increases as compared to the BG absorption image $I_{AB\_BG}(x,y)$ obtained in BG radiographing of the related art. In the present invention, since the image unevenness is removed by correcting only the high-frequency component of a BG absorption image $I_{AB\_BG}(x,y)$ obtained by BG radiographing of the related art, the image unevenness can be removed without lowering the image quality.

Note that an example of an image obtained by taking the natural logarithm of the absorption image $I_{AB}(x,y)$ is shown in FIGS. 10A and 10B. An X-ray image is typically an image (corresponding to an absorption image herein) showing the transmittance of X-rays through the subject, which is obtained by taking the natural logarithm so as to be displayed according to a value proportional to the thickness of the subject. In the following description, a process of obtaining a corrected absorption image $I_{AB2}(x,y)$ in which the image unevenness remaining in the absorption image $I_{AB}(x,y)$ is reduced will be presented. If the image unevenness of the corrected absorption image $I_{AB2}(x,y)$ is reduced, the image unevenness is also reduced in an image obtained by taking the natural logarithm. An example of an image obtained by taking the natural logarithm of an absorption image that is a typical way of display will therefore be presented as an image having the advantageous effects of the process of the present embodiment (see FIGS. 13A, 14A, 15, and 16).

Hereinafter, an absorption image generation process including correction of the proportion of the high-frequency component of the BG absorption image $I_{AB\_BG}(x,y)$ will be described. FIG. 11 shows a flowchart of the absorption image generation process performed by the control unit 51 of the controller 5. The absorption image generation process is performed by cooperation of the control unit 51 and programs stored in the storage unit 55.

First, the control unit 51 generates a subject absorption image $I_{AB\_SAMPLE}(x,y)$ on the basis of a series of subject moire fringe images received by the communication unit 54, and generates a BG absorption image $I_{AB\_BG}(x,y)$ on the basis of a series of BG moire fringe images received by the communication unit 54 (step S11).

In step S11, the subject absorption image $I_{AB\_SAMPLE}(x,y)$ is generated with use of [Expression 2] described above, and the BG absorption image $I_{AB\_BG}(x,y)$ is generated with use of [Expression 3] described above. Note that the moire fringe images are preferably subjected to offset correction, gain correction, defective pixel correction, and the like in advance.

Subsequently, the control unit 51 extracts the high-frequency component of the BG absorption image $I_{AB\_BG}(x,y)$ (step S12).

The high-frequency component of the BG absorption image $I_{AB\_BG}(x,y)$ represents the proportion of fine unevenness structure in the BG absorption image $I_{AB\_BG}(x,y)$ to an average value of surrounding pixels. In step S12, first, the BG absorption image $I_{AB\_BG}(x,y)$ is averaged by the surrounding pixels or filtering with a Gaussian filter or the like for blurring is conducted, for example, so that a low-frequency component $L_{AB\_BG}(x,y)$ of the BG absorption image $I_{AB\_BG}(x,y)$ is obtained. Subsequently, a high-frequency component $H_{AB\_BG}(x,y)$ is extracted on the basis of the BG absorption image $I_{AB\_BG}(x,y)$ and the low-frequency component $L_{AB\_BG}(x,y)$. Here, the BG absorption image $I_{AB\_BG}(x,y)$ is divided by the low-frequency component $L_{AB\_BG}(x,y)$, so that an image with pixel values of 1+high-frequency component (a high-frequency component expressed on the basis of pixel values 1) is obtained. That is, the high-frequency component $H_{AB\_BG}(x,y)$ of the BG absorption image $I_{AB\_BG}(x,y)$ can be extracted according to the following [Expression 4]:

High-frequency component $H_{AB\_BG}(x,y)=$
(BG absorption image $I_{AB\_BG}(x,y)$/Low-frequency component $L_{AB\_BG}(x,y)$)−1 [Expression 4]

Subsequently, the control unit 51 corrects the proportion of the high-frequency component $H_{AB\_BG}(x,y)$ of the BG absorption image $I_{AB\_BG}(x,y)$ (step S13).

A corrected BG absorption image $I_{AB\_BG2}(x,y)$ where the proportion of the high-frequency component of the BG absorption image $I_{AB\_BG}(x,y)$ is corrected to that of the subject absorption image $I_{AB\_SAMPLE}(x,y)$ may be obtained from an expression of multiplying the high-frequency component $H_{AB\_BG}(x,y)$ of the left side of [Expression 4] by a coefficient $a(x,y)$ for correcting the proportion of the high-frequency component to that of the subject absorption image $I_{AB\_SAMPLE}(x,y)$. That is, the corrected BG absorption image $I_{AB\_BG2}(x,y)$ where only the proportion of the high-frequency component can be obtained by the following [Expression 5]:

Corrected BG absorption image $I_{AB\_BG2}(x,y)$=Low-frequency component $L_{AB\_BG}(x,y) \times (1+a(x,y) \times$ High-frequency component $H_{AB\_BG}(x,y))$ [Expression 5]

Subsequently, the control unit 51 performs a BG process using the corrected BG absorption image $I_{AB\_BG2}(x,y)$ (step S14). Specifically, the image unevenness of the subject absorption image $I_{AB\_SAMPLE}(x,y)$ is corrected by dividing the subject absorption image $I_{AB\_SAMPLE}(x,y)$ by the corrected BG absorption image $I_{AB\_BG2}(x,y)$. As a result, a corrected absorption image $I_{AB2}(x,y)$ with reduced image unevenness is generated.

Note that the coefficient $a(x,y)$ used in step S13 is preferably set to a value corresponding to the pixel values of the absorption image $I_{AB}(x,y)$ resulting from the BG process. In the case of subjects having the same material, as the thickness of the subject is greater, absorption of X-rays increases and the X-ray spectral variation thus becomes larger. As described above, the proportion of the high-frequency component caused by the image unevenness of the subject absorption image $I_{AB\_SAMPLE}(x,y)$ varies depending on the difference in X-ray spectrum. It is thus preferable that the coefficient $a(x,y)$ be set to a value corresponding to the pixel values of the absorption image $I_{AB}(x,y)$ resulting from the BG process indicating a value corresponding to the thickness of the subject when the subject is of the same material. Since the influence of the image unevenness on the pixel values is small in the absorption image $I_{AB}(x,y)$ resulting from the BG process, there is no problem in determining $a(x,y)$ on the basis of the pixel values of the absorption image $I_{AB}(x,y)$ resulting from the BG process of the related art obtained by dividing the subject absorption image $I_{AB\_SAMPLE}(x,y)$ by an uncorrected BG absorption image $I_{AB\_BG}(x,y)$.

Furthermore, the coefficient $a(x,y)$ is preferably set for each group of materials of the subject making similar X-ray spectral changes. This is because different subject materials result in different X-ray spectra after passing through the subjects even if the pixel values of the absorption image $I_{AB}(x,y)$ are the same, and the proportion of the high-frequency component caused by the image unevenness of the subject absorption image $I_{AB\_SAMPLE}(x,y)$ will thus be different.

Furthermore, the image unevenness of the subject absorption image $I_{AB\_SAMPLE}(x,y)$ and the BG absorption image $I_{AB\_BG}(x,y)$ caused by a grating includes unevenness in stripes (vertical stripes) and unevenness in particles, and both of the unevennesses cannot be corrected with high accuracy by using one coefficient $a(x,y)$. The coefficient $a(x,y)$ is therefore preferably set individually for correcting unevenness in stripes and for correcting unevenness in particles.

Figure 12A:
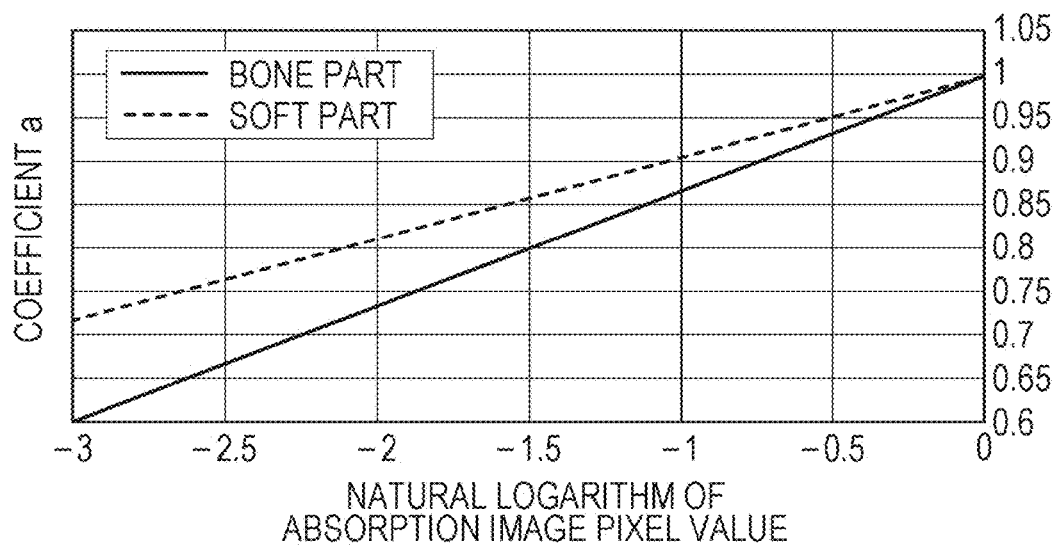
FIG. 12A is a graph showing a correction coefficient for correcting unevenness in stripes.
Figure 12B:
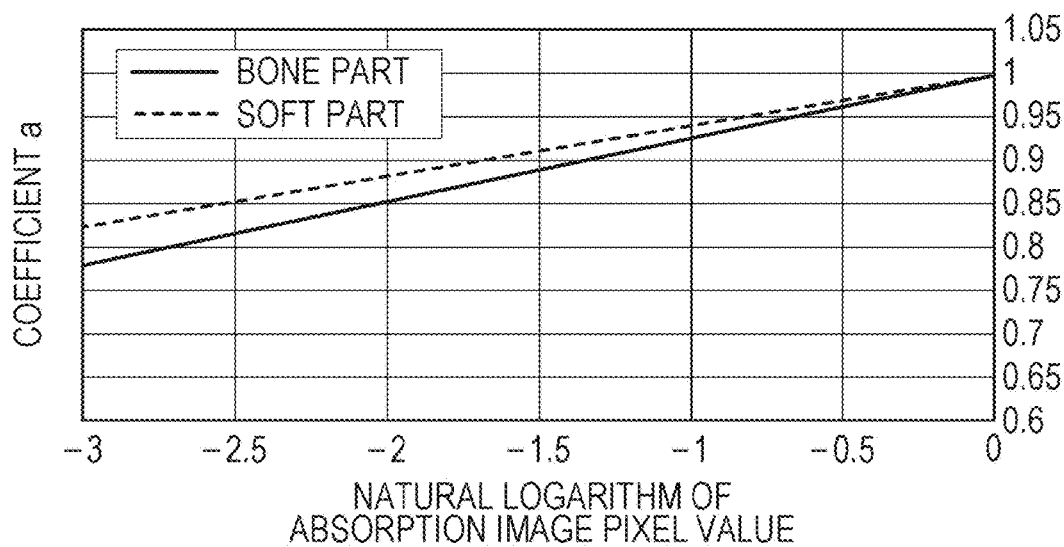
FIG. 12B is a graph showing a correction coefficient for correcting unevenness in particles.

Thus, in the present embodiment, as shown in FIGS. 12A and 12B, coefficients a are provided individually for correcting unevenness in stripes (see FIG. 12A) and for correcting unevenness in particles (see FIG. 12B), and the values of the respective coefficients a(x,y) associated with pixel values (or values obtained by taking the natural logarithm thereof) of the absorption image $I_{AB}(x,y)$ resulting from the BG process are prestored in the storage unit 55 in a form of functions or in a table for each of the subject materials (herein, a bone part and a soft part or soft tissue). In step S13 of FIG. 11, the control unit 51 then obtains and sets a coefficient a(x,y) associated with the pixel values (or a value obtained by taking the natural logarithm thereof) of the absorption image $I_{AB}(x,y)$ resulting from the BG process on the basis of the function or the table stored in the storage unit 55. Note that the coefficients a in FIGS. 12A and 12B are obtained experimentally and empirically. Specifically, the relation between a coefficient a with which the image unevenness of the absorption image $I_{AB}(x,y)$ is attenuated the most for a material such as acryl or aluminum and the pixel values $I_{AB}(x,y)$ of the absorption image is obtained first. A coefficient a with which the unevenness remaining in the absorption image $I_{AB}(x,y)$ acquired by radiographing a phantom of the bone part and the soft part or an actual part to be radiographed is eliminated the most is generated on the basis of the data. For example, regarding the coefficients shown in FIGS. 12A and 12B, a coefficient a obtained for acryl is applied to the coefficient a for a soft part, and an average value of coefficients a obtained for acryl and aluminum is applied to the coefficient a for a bone part. Such a method of obtaining the coefficient a is not limited to a bone part and a soft part described above but is useful for human bodies.

Figure 13A:
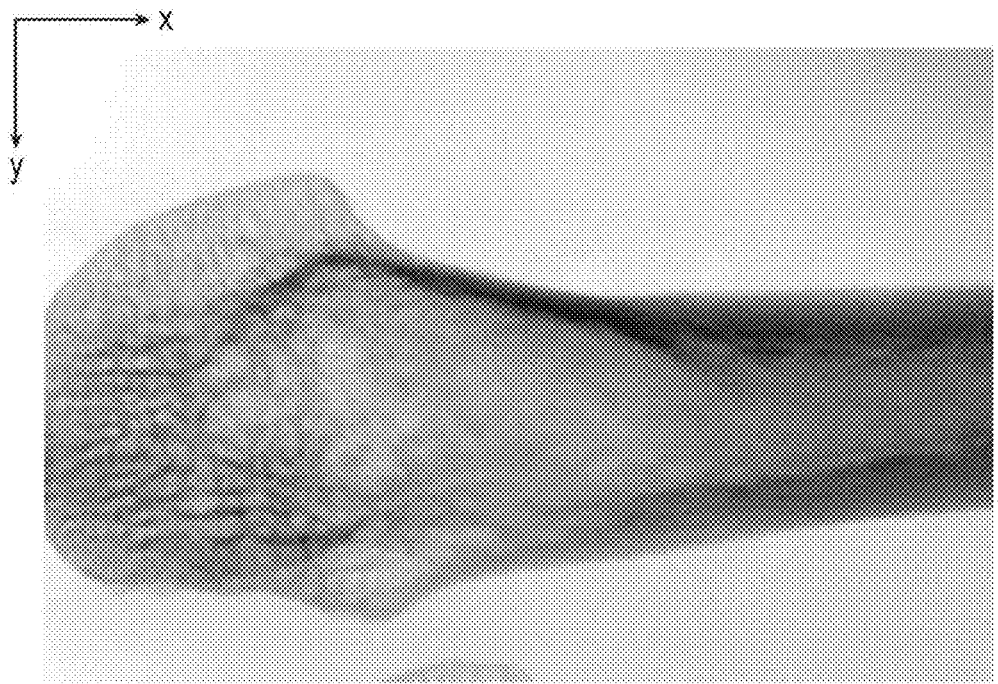
FIG. 13A is an image obtained by taking a natural logarithm of a corrected absorption image generated by using a correction coefficient for soft tissue on the entire image.
Figure 13B:
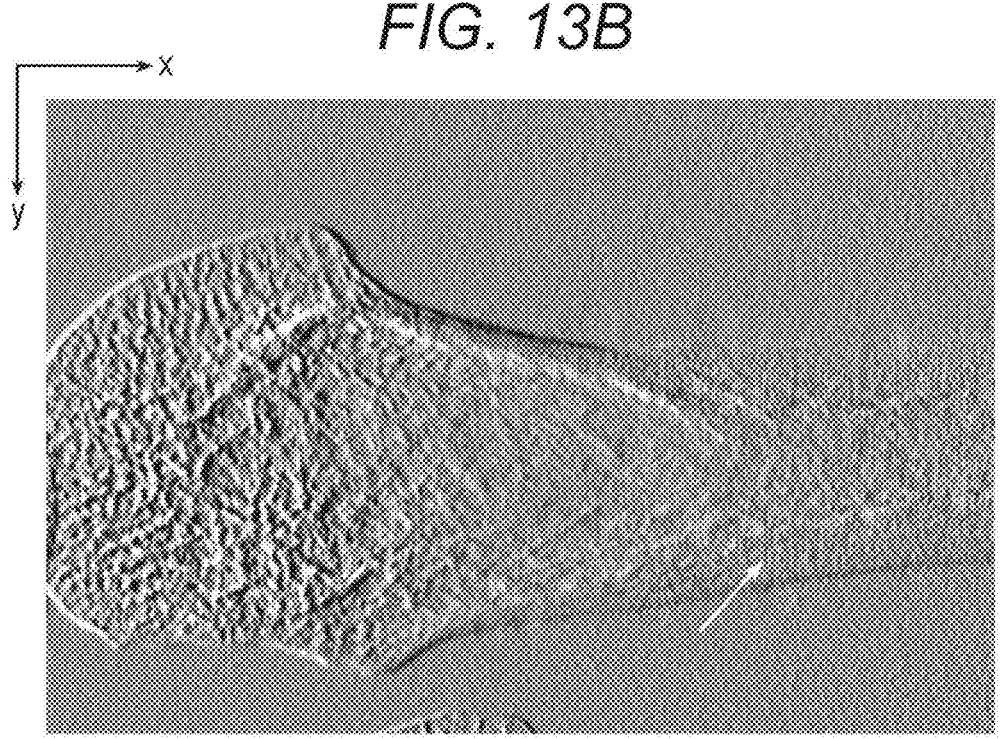
FIG. 13B is a differential absorption image of the image of FIG. 13A.

FIG. 13A is an image obtained by taking the natural logarithm of a corrected absorption image $I_{AB2}(x,y)$ generated by using a coefficient a(x,y) for soft tissue on the entire image in generating the corrected absorption image $I_{AB2}(x,y)$ on the basis of the subject absorption image $I_{AB\_SAMPLE}(x,y)$ shown in FIG. 8 and the BG absorption image $I_{AB\_BG}(x,y)$ shown in FIG. 9. FIG. 13B is a differential absorption image calculated by subtracting pixel values of pixels adjacent to both sides of each of the pixels in the x direction (left-right direction on the drawing sheet) of the image of FIG. 13A.

Figure 14A:
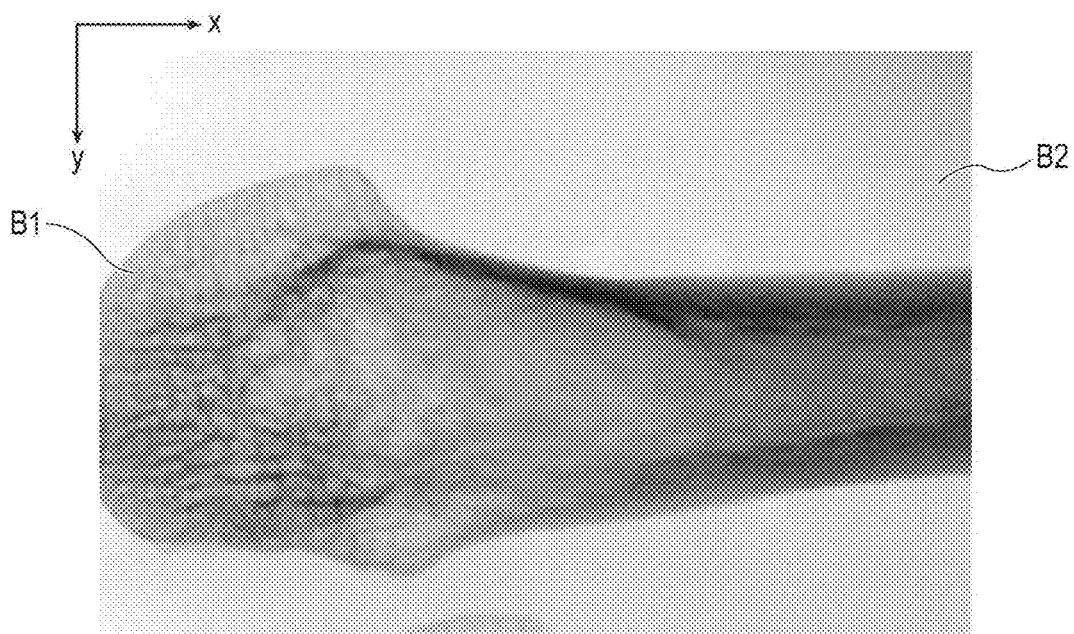
FIG. 14A is an image obtained by taking a natural logarithm of a corrected absorption image generated by using a correction coefficient for a bone part on a bone part area and using a correction coefficient for soft tissue on a soft part area.
Figure 14B:
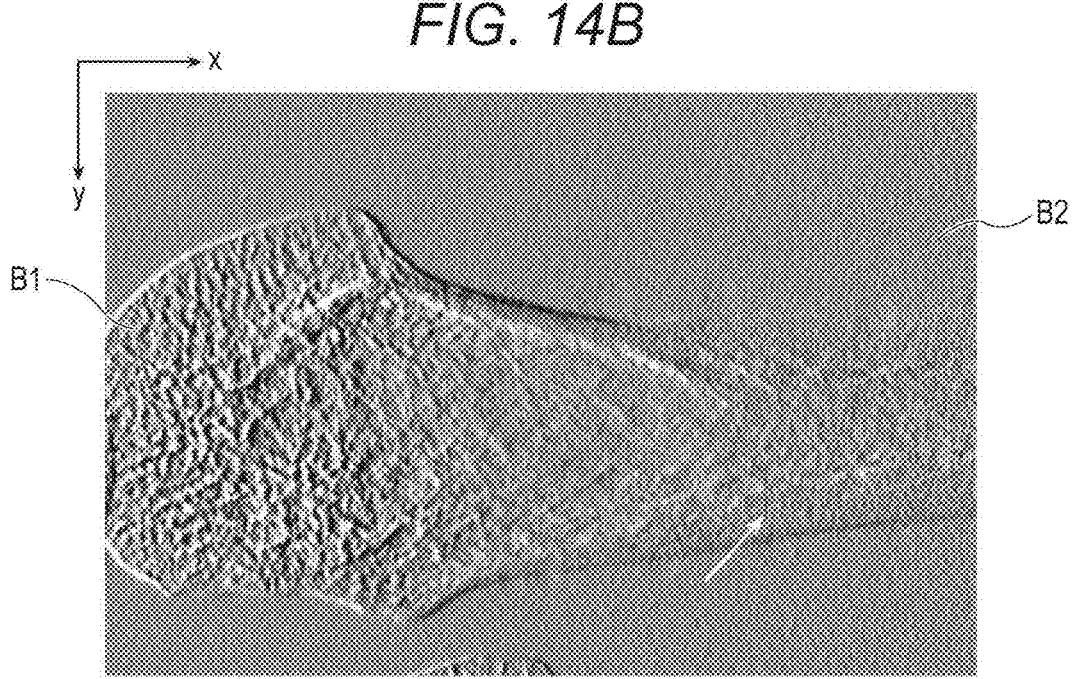
FIG. 14B is a differential absorption image of the image of FIG. 14A.

FIG. 14A is an image obtained by taking the natural logarithm of a corrected absorption image $I_{AB\_BG}(x,y)$ generated by using a coefficient a(x,y) for bone part on a bone part area B1 and a coefficient a(x,y) for soft tissue on a soft part area B2 in generating the corrected absorption image $I_{AB2}(x,y)$ on the basis of the subject absorption image $I_{AB\_SAMPLE}(x,y)$ shown in FIG. 8 and the BG absorption image $I_{AB\_BG}(x,y)$ shown in FIG. 9. FIG. 14B is a differential absorption image calculated by subtracting pixel values of pixels adjacent to both sides of each of the pixels in the x direction (left-right direction on the drawing sheet) of the image of FIG. 14A.

Note that FIGS. 13A and 14A are generated by using a coefficient a for correcting unevenness in stripes shown in FIG. 12A for unevenness in stripes and using a coefficient a for correcting unevenness in particles shown in FIG. 12B for unevenness in particles, respectively.

As shown in FIGS. 13A and 13B, when the entire image is corrected by using a coefficient a(x,y) for soft tissue, it can be seen that the unevenness in stripes and the unevenness in particles are both attenuated as compared to those in FIGS. 10A and 10B generated according to the technique of the related art but that the unevenness in stripes remains in the bone part (see an arrow in FIG. 13B, for example). In contrast, when coefficients a(x,y) for bone part and for soft tissue are used to correct the bone part area B1 and to correct the soft part area B2, respectively, it can be seen that the unevenness in vertical stripes can also be reduced in the bone part as shown in FIGS. 14A and 14B.

Note that the bone part area B1 and the soft part area B2 can be distinguished from each other by setting a threshold for pixel values of small-angle scattering images $I_{sc}(x,y)$ generated from the same moire fringe images $I_{sc}(x,y)$ and distinguishing those smaller than the threshold as being the bone part and those larger than the threshold as being the soft part. The small-angle scattering image $I_{sc}(x,y)$ can be obtained by the following [Expression 6]:

[Formula 4]

$$I_{SC}(x, y) = \frac{I_{SC\_SAMPLE}(x, y)}{I_{SC\_BG}(x, y)} \qquad \text{[Expression 6]}$$

where

[Formula 5]

$$I_{SC\_SAMPLE}(x, y) = \frac{2 \times \left| \sum_{k=0}^{M-1} I_k^{SAMPLE}(x, y) \exp\left(-\frac{i2\pi k}{M}\right) \right|}{I_{AB\_SAMPLE}(x, y)} \qquad \text{[Expression 7]}$$

[Formula 6]

$$I_{SC\_BG}(x, y) = \frac{2 \times \left| \sum_{k=0}^{M-1} I_k^{BG}(x, y) \exp\left(-\frac{i2\pi k}{M}\right) \right|}{I_{AB\_BG}(x, y)} \qquad \text{[Expression 8]}$$

$I_{sc\_SAMPLE}(x,y)$ and $I_{sc\_BG}(x,y)$ represent pixel values of the subject small-angle scattering image and the BG small-angle scattering image, respectively.

Figure 15:
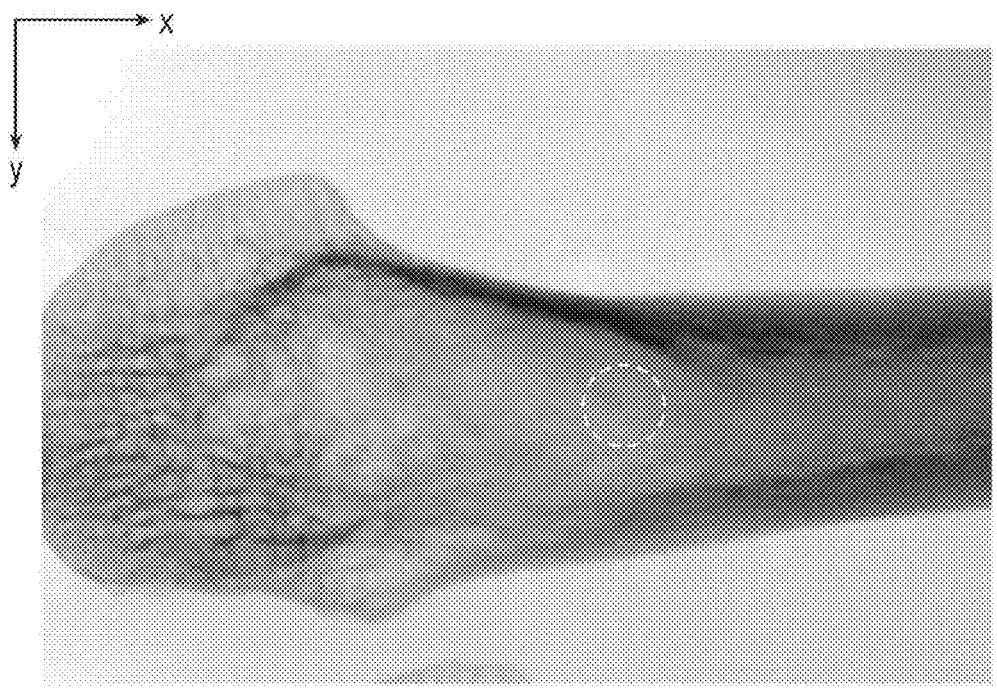
FIG. 15 is an image obtained by taking a natural logarithm of a corrected absorption image generated by using a correction coefficient for correcting unevenness in stripes on the entire image.
Figure 16:
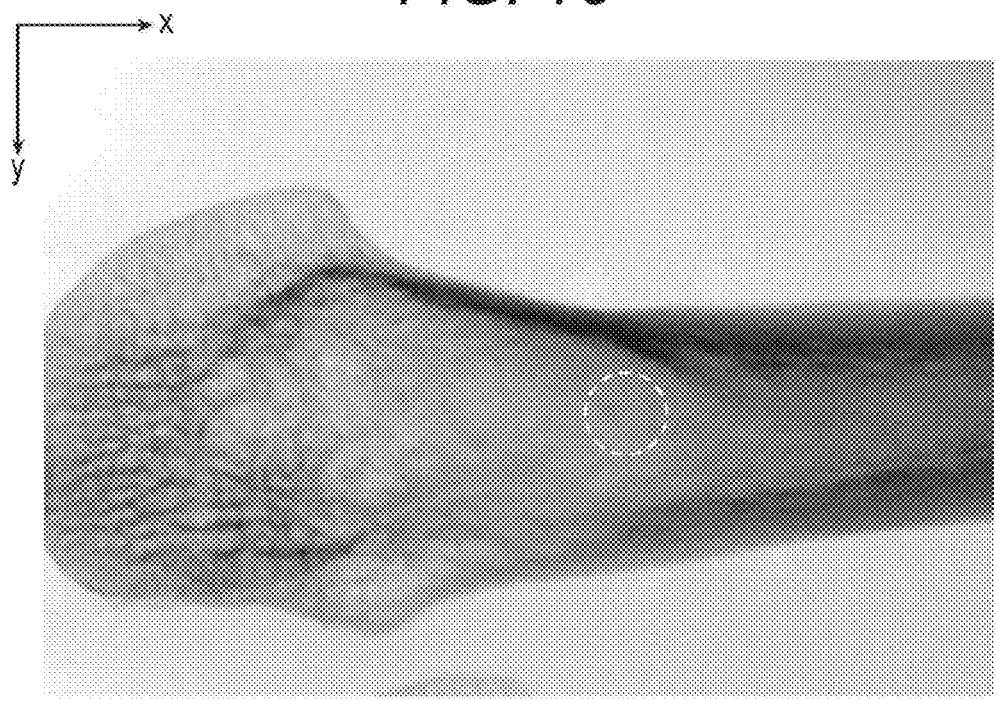
FIG. 16 is an image obtained by taking a natural logarithm of a corrected absorption image generated by using a correction coefficient for correcting unevenness in stripes on unevenness in stripes and using a correction coefficient for correcting unevenness in particles on unevenness in particles.

Furthermore, FIG. 15 is an image obtained by taking the natural logarithm of a corrected absorption image $I_{AB2}(x,y)$ generated by using a coefficient a(x,y) for correcting unevenness in stripes on the entire image in generating the corrected absorption image $I_{AB2}(x,y)$ from the subject absorption image $I_{AB\_SAMPLE}(x,y)$ shown in FIG. 8 and the BG absorption image $I_{AB\_BG}(x,y)$ shown in FIG. 9. FIG. 16 is an image obtained by taking the natural logarithm of a corrected absorption image generated by using a coefficient a(x,y) for correcting unevenness in stripes on unevenness in stripes and a coefficient a(x,y) for correcting unevenness in particles on unevenness in particles in generating the corrected absorption image $I_{AB2}(x,y)$ from the subject absorption image $I_{AB\_SAMPLE}(x,y)$ shown in FIG. 8 and the BG absorption image $I_{AB\_BG}(x,y)$ shown in FIG. 9.

Note that FIGS. 15 and 16 are generated by using a coefficient a for a bone part on a bone part and a coefficient a for soft tissue on a sort part.

In the image obtained by taking the natural logarithm of the absorption image $I_{AB}(x,y)$ resulting from the BG process shown in FIG. 10A, the particle-like structure seen in an area in a broken line is depicted as being white as compared to the surroundings, while the particle-like structure is depicted as being black in FIG. 15. This means that excessive correction is made because the coefficient a(x,y) appropriate for the unevenness in stripes has a smaller value than the coefficient a(x,y) appropriate for the unevenness in particles (see FIGS. 12A and 12B). Thus, the image unevenness in particles can be appropriately corrected as shown in FIG. 16 by setting different coefficients a(x,y) for the unevenness in stripes and the unevenness in particles.

The unevenness in stripes and the unevenness in particles can be distinguished from each other by comparing the value of a high-frequency component $H_{AB\_BG}(x,y)$ calculated according to [Expression 4] with a predetermined threshold. As can be seen from the grayscale of the unevenness in stripes and the unevenness in particles depicted in the BG absorption image $I_{AB\_BG}(x,y)$ in FIG. 9 the unevenness in particles varies more greatly in pixel values than the surrounding area. That is, the value of the high-frequency component $H_{AB\_BG}(x,y)$ is small (although the absolute value is large, the value is small relative to the pixel values of surrounding pixels). Thus, unevenness can be distinguished as being unevenness in particles when the value of the high-frequency component $H_{AB\_BG}(x,y)$ calculated according to [Expression 4] is smaller than a predetermined threshold and as being unevenness in stripes when the value is equal to or larger than the threshold.

As described above, the control unit 51 of the controller 5 generates a subject absorption image $I_{AB\_SAMPLE}(x,y)$ on the basis of subject moire fringe images acquired by the X-ray equipment 1, generates a BG absorption image $I_{AB\_BG}(x,y)$ on the basis of the BG moire fringe images, corrects the proportion of the high-frequency component in the BG absorption image $I_{AB\_BG}(x,y)$, and uses the resulting corrected BG absorption image $I_{AB\_BG2}(x,y)$ to correct the subject absorption image to generate a corrected absorption image $I_{AB2}(x,y)$. The correction of the proportion of the high-frequency component in the BG absorption image $I_{AB\_BG}(x,y)$ is conducted by extracting a high-frequency component $H_{AB\_BG}(x,y)$ in units of pixels of the BG absorption image $I_{AB\_BG}(x,y)$, and multiplying the high-frequency component $H_{AB\_BG}(x,y)$ by a coefficient a (x,y) for correcting the high-frequency component to the subject absorption image $I_{AB\_SAMPLE}(x,y)$, for example.

Thus, since the BG process is conducted after correcting the proportion of the image unevenness to pixel values of the BG absorption image $I_{AB\_BG}(x,y)$ to that of the subject absorption image $I_{AB\_SAMPLE}(x,y)$, the image unevenness can be reduced with high accuracy from the subject absorption image $I_{AB\_SAMPLE}(x,y)$. Furthermore, since a member for causing X-ray spectral variation equivalent to that of the subject need not be placed in BG radiographing unlike the related art, the image unevenness can be reduced easily without trouble.

The coefficient a(x,y) is preferably set on the basis of a generated absorption image $I_{AB}(x,y)$ resulting from the BG process of the related art. As a result, the BG absorption image $I_{AB\_BG}(x,y)$ can be corrected with high accuracy according to the thickness of the subject.

Furthermore, different coefficients a(x,y) are preferably set between an area corresponding to a bone part area and an area corresponding to a soft part area in the subject absorption image $I_{AB\_SAMPLE}(x,y)$. As a result, corrections suitable for the bone part area and the soft part area, respectively, can be conducted.

Furthermore, the coefficient a(x,y) is preferably set according to the value of a high-frequency component of each of the pixels in the BG absorption image $I_{AB\_BG}(x,y)$. As a result, both of unevenness in stripes and unevenness in particles can be corrected with high accuracy.

The description of the embodiment above provides preferable examples according to the present invention, and the present invention is not limited thereto.

For example, while an example of X-ray equipment having a Talbot-Lau interferometer in which the multislit 12 is shifted relative to the first grating 14 and the second grating 15 in radiographing has been described in the embodiment, the present invention may also be applied to X-ray equipment having a Talbot-Lau interferometer in which any one or two of the multislit 12, the first grating 14, and the second grating 15 are shifted. Furthermore, the present invention may be applied to X-ray equipment having a Talbot interferometer in which either one of the first grating 14 and the second grating 15 is shifted with respect to the other gratings.

Furthermore, while an example of a medical image system in which the multislit 12, the first grating 14, and the second grating 15 are one-dimensional gratings has been described in the embodiment, the present invention may also be applied to a medical image system in which a two-dimensional grating is used to perform fringe scanning in a two-dimensional manner.

Furthermore, while a case in which three types of reconstructed images are generated has been described in the embodiment, the present invention may be applied to any medical image system that generates at least an absorption image.

Still further, detailed features and detailed operations of respective devices included in the medical image system may be modified as appropriate without departing from the gist of the invention.

Although the present invention has been described and illustrated in detail, it is clearly understood that the same is by way of illustrated and example only and is not to be taken by way of limitation, the scope of the present invention being interpreted by terms of the appended claims.

What is claimed is:

1. An image processing system comprising:
   (i) X-ray equipment having a Talbot interferometer or a Talbot-Lau interferometer, the X-ray equipment including:
   an X-ray source configured to emit X-rays;
   a plurality of gratings arranged in an emitting direction of the X-rays, each of the plurality of gratings having a plurality of slits arranged in a direction perpendicular to the emitting direction of the X-rays; and
   an X-ray detector irradiated by the X-ray source, the X-ray detector having conversion elements for accumulating charge according to X-rays having passed through the plurality of gratings and generating electrical signals, the conversion elements being arranged two-dimensionally, and the X-ray detector being configured to read the electrical signals generated by the conversion elements to acquire a moire fringe image; and
   (ii) a controller which includes a CPU and a memory, the CPU being configured to execute stored programs to perform operations including:
   generating a subject absorption image based on moire fringe images containing a subject that are acquired by placing the subject on a subject placement position provided on an emission path of the X-rays and emitting X-rays from the X-ray source;
   generating a subjectless absorption image based on subjectless moire fringe images acquired by emitting X-rays from the X-ray source with no subject placed at the subject placement position provided on the emission path of the X-rays;
   correcting image unevenness of the subject absorption image by using the subjectless absorption image; and
   correcting a proportion of a high-frequency component in the subjectless absorption image to obtain a corrected subjectless absorption image, wherein the correcting of the image unevenness of the subject absorption image is performed using the corrected subjectless absorption image.

2. The image processing system according to claim 1, wherein the correcting the proportion of the high-frequency component in the subjectless absorption image comprises extracting the high-frequency component in units of pixels of the subjectless absorption image, and multiplying the high-frequency component by a correction coefficient for correcting the high-frequency component to that of the subject absorption image.

3. The image processing system according to claim 2, wherein the correcting the proportion of the high-frequency component in the subjectless absorption image comprises setting a correction coefficient for each pixel in the subjectless absorption image according to a value of a corresponding pixel of an image obtained by correcting the subject absorption image by using the subjectless absorption image before being corrected.

4. The image processing system according to claim 2, wherein the correcting the proportion of the high-frequency component in the subjectless absorption image comprises setting different correction coefficients between an area corresponding to a bone part area and an area corresponding to a soft part area in the subject absorption image.

5. The image processing system according to claim 2, wherein the correcting the proportion of the high-frequency component in the subjectless absorption image comprises setting a correction coefficient for each pixel in the subjectless absorption image according to a value of the high-frequency component of the pixel in the subjectless absorption image.

6. The image processing system according to claim 1, wherein the correcting of the image unevenness of the subject absorption image comprises dividing the subject absorption image by the corrected subjectless absorption image.

7. An image processing device for performing image processing on an image acquired by X-ray equipment having a Talbot interferometer or a Talbot-Lau interferometer, the image processing device comprising:
 a controller which includes a CPU and a memory, the CPU being configured to execute stored programs to perform operations including:
 generating a subject absorption image based on moire fringe images containing a subject that are acquired by placing the subject on a subject placement position provided on an emission path of X-rays in the X-ray equipment and emitting X-rays;
 generating a subjectless absorption image based on subjectless moire fringe images acquired by emitting X-rays with no subject placed at the subject placement position provided on the emission path of the X-rays in the X-ray equipment;
 correcting a proportion of a high-frequency component in the subjectless absorption image to obtain a corrected subjectless absorption image; and
 correcting image unevenness of the subject absorption image by using the corrected subjectless absorption image.

* * * * *